US007855317B2

(12) United States Patent  (10) Patent No.:     US 7,855,317 B2
Langham                          (45) Date of Patent:     Dec. 21, 2010

(54) NON-DEHISCENT SESAME VARIETY SESACO 32

(75) Inventor: Derald Ray Langham, San Antonio, TX (US)

(73) Assignee: Sesaco Corporation, Fallbrook, CA (US)

( * ) Notice: Subject to any disclaimer, the term of this patent is extended or adjusted under 35 U.S.C. 154(b) by 479 days.

(21) Appl. No.: 12/041,205

(22) Filed: Mar. 3, 2008

(65)            Prior Publication Data

US 2009/0222939 A1     Sep. 3, 2009

(51) Int. Cl.
  A01H 1/00   (2006.01)
  A01H 5/00   (2006.01)
  A01H 5/10   (2006.01)
  C12N 5/04   (2006.01)
(52) U.S. Cl. ................... 800/260; 800/296; 800/298; 435/430; 435/430.1
(58) Field of Classification Search .............. None
See application file for complete search history.

(56)            References Cited

U.S. PATENT DOCUMENTS

| 6,100,452 | A | 8/2000 | Langham |
| 6,781,031 | B2 | 8/2004 | Langham |
| 6,815,576 | B2 | 11/2004 | Langham |
| 7,148,403 | B2 | 12/2006 | Langham |
| 7,332,652 | B2 | 2/2008 | Langham |
| 2006/0230472 | A1* | 10/2006 | Langham ............... 800/295 |

FOREIGN PATENT DOCUMENTS

| WO | WO9915681 | 4/1999 |
| WO | WO0013488 | 3/2000 |

OTHER PUBLICATIONS

Ashri, A. 1998. "Sesame Breeding," Plant Breeding Rev. 16:179-228.
Ashri, A. 1980. "Sesame," Oil Crops of the World, Chap. 18, pp. 375-387; McGraw-Hill Publishing, Co., New York.
Bakheit, et al. 1996. "Inheritance of Some Qualitative and Quantitative Characters in Sesamum idicum L," Assuit Journal of the Agricultural Sciences 27:27-41.
Day, Jamie. 1998 "The mechanism of indehiscence in Sesame. Features that might be useful in a breeding programme," Third FAO/IAEA Research Coordination meeting on Induced, pp. 1-16.
Mutations for Sesame Improvements, Bangkok, Thailand; Apr. 6-19, 1998; 11pp.
Delgado, et al. 1992. "Analisis Del Cruzamiento Dialelico De Seis Variedades Indehiscentes Y Dos Dehiscentes de Ajonjoli *Sesamum indicum* L." Agronomia Tropical 42:191-210.
Hutson, B.D. 1983. "Standards for the inspection and grading of sesame seed," Hutson Laboratories, Yuma, Arizona, pp. 1-5.
IBPGR Secretariat. 1981. "Descriptors for Sesame," International Board for Plant Genetic Resources, Rome, pp. 1-19.
Kalton, R.R. 1949. "A promising new oilseed crop for Texas," Proc First International Sesame Conference, Clemson Agricultural College, Clemson, South Carolina, pp. 62-66.

Langham, D.R. 2007. "Phenology of Sesame," Issues in New Crops and New Uses, Janick & Whipkey, eds., ASHS Press, Alexandria, VA, pp. 144-182.
Langham, D.G. 1944. "Natural and controlled pollination in sesame," Journal of Heredity 8:254-256.
Langham, D.G. And Rodriguez, J. 1949. "Improvements in Sesame in Venezuela," Proc. First Intern'l Sesame Conf., Clemson Agri. College, Clemson, South Carolina, pp. 74-79.
Langham, et al. 1956. "Dehiscencia Y otras caracteristicas del ajonjoli, *Sesamum indicum* L., en relacion con el problema de la cosecha," Gensa, Maracay, Venezuela; pp. 3-16.
Langham, D.R. 1998. "Shatter resistance in Sesame," Third FAO/IAEA Res. Co-ord. Mtng on induced Mutations for Sesame Improvements, Bangkok, Thailand, Apr. 6-10, 1998; 14 pages.
Langham, D.R. 2001. "Shatter resistance in sesame," In: L. Van Zanten (ed.), Sesame improvements by induced mutations, Proc. Final FAO/IAEA Coordinationp °search Meeting, pp. 1-12, IAEA, Vienna TECDOC 1195, pp. 51-61.
Langham, D.R. & Wimers, T. 2002. "Progress in mechanizing sesame in the U.S. through breeding," Trends in Crops and New Uses, J. Janick & A. Whipkey (eds.), ASHA Press Alexandria, VA; pp. 157-173.
Namiki, Mitsuo. 1995. "The Chemistry and Physiological Functions of Sesame," Food Reviews International, 11:281-329.
Osman, H.E. 1985. "Studies in sesame: hybridization and related techiniques," FAO Plant Production and Protection Paper No. 66, pp. 145-156.
"Recommendations for the Discussion Groups," 1995. Proceedings of Sesame Workshop, Darwin and Katherine, Northern Territory, Australia, Mar. 12-23, 1995, pp. 252-257.
Shigeo, et al. 1994. "Breeding of good quality sesame with dehiscence resistance and strong antioxidative property," Baiorunessansu Keikaku (abstract only).
Wongyai, W. & Juttpornpong, S. 1992 "Indirect selection for seed weight in sesame using capsule size as a criteria," Sesame and Safflower Newsletter, No. 7, pp. 4-7.
Weiss, E.A. 1971. "History," Castor, Sesame and Safflower, Leonard-Hill Books, London; pp. 311-525.
Weiss, E.A. 1983. "Sesame," Oilseed Crops, Longman Inc., New York, pp. 282-340.
Weiss. 2000. "Sesame," Oilseed Crops, Longman Inc., New York, pp. 131-164.
Yermanos, D.M. 1980. "Sesame," Hybridization of Crop Plants, American Society of Agronomy—Crop Science of America, Madison, Wisconsin, pp. 549-563.
Yermanos, D.M. 1984. "Sesame growing: an idealized overview," Text of speech given in Cairo, Egypt, 4 pages.
Zanten, L.Van (ed.) 1996. "Conclusions and Recommendations," 2nd FAO/IAEA Research Coordination Meeting, Antalya, Turkey, pp. 107-113.

* cited by examiner

*Primary Examiner*—Vinod Kumar
(74) *Attorney, Agent, or Firm*—Eugenia S. Hansen; Hemingway & Hansen, LLP

(57)            ABSTRACT

Improved non-dehiscent sesame (*Sesamum indicum* L.) designated Sesaco 32 (S32) is herein disclosed. Its degree of shatter resistance, or seed retention, makes S32 suitable for mechanized harvesting.

9 Claims, 7 Drawing Sheets

```
                                /G8  (1)
                           /804 (17)
                        |    |    /111  (2)
                        |    \111X (12)
                        |          \BEE
                   /K0338 (22)
                  |    |    /191  (3)
                  |    \96B (13)
                  |          \BEE
             /ZSA (27)
            |    |    /G8  (1)
            |    \S11 (18)
            |         |    /111  (2)
            |         \111X (12)
            |               \BEE
       /SAA (30)            /G8  (1)
      |    |           /B043 (14)
      |    |          |    \MEL  (4)
      |    |      /C063 (19)
      |    |     |    \G54  (5)
      |    \233 (23)
      |          \193  (6)
 /13H (32)            /111  (2)
|    |           /111X (12)
|    |          |     \BEE
|    |      /F820 (20)
|    |     |    \104  (7)
|    |    /578 (24)
|    |   |    |    /104  (7)
|    |   |    \F853 (15)
|    |   |          \192  (8)
|    \031 (28)
|         \118  (9)
S32 (33)       /G8  (1)
|          /804 (17)
|         |    |    /111  (2)
|         |    \111X (12)
|         |          \BEE
|    /56B (25)
|   |    |    /111  (2)
|   |    |    /F822 (16)
|   |    |   |    \192  (8)
|   |    \562 (21)
|   |         \700 (10)
\2CB (31)
    |         /702 (11)
    |    /L6651 (26)
    |   |    |    /G8  (1)
    \2CA (29) \804 (17)
         |         |    /111  (2)
         |         \111X (12)
         |               \BEE
         |    /G8  (1)
         \S11 (18)
              |    /111  (2)
              \111X (12)
                    \BEE
```

FIG. 1

NON-DEHISCENT SESAME VARIETY SESACO 32

CROSS REFERENCE TO RELATED APPLICATIONS

Not applicable.

STATEMENT REGARDING FEDERALLY SPONSORED RESEARCH OR DEVELOPMENT

Not applicable.

TECHNICAL FIELD

This invention relates to a new *Sesamum indicum* L. variety with improved non-dehiscence appropriate for mechanized harvesting.

BACKGROUND OF THE INVENTION

Sesame, or *Sesamum indicum*, is a tropical annual cultivated worldwide for its oil and its nut flavored seeds. The sesame plant grows to a height of about 56-249 cm, and at its leaf axils are found capsules which contain the sesame seed. Upon maturity in nature, the capsules holding the sesame seeds begin to dry down, the capsules normally split open, and the seeds fall out. Commercially, the harvester tries to recover as much seed as possible from mature capsules. From ancient times through the present, the opening of the capsule has been the major factor in attempting to successfully collect the seed. Harvesting methods, weather, and plant characteristics all contribute to the amount of seed recovered.

The majority of the world's sesame is harvested manually. With manual non-mechanized methods, it is desirable for the sesame seed to fall readily from the plant. Upon physiological maturity, the sesame stalks are cut, tied into small bundles, and then stacked in shocks. Further harvesting procedures vary from country to country and from area to area within countries. Some move the shocks to a threshing floor so that the seed that falls out can be recovered. Others put plastic or cloth in the fields under the shocks to catch the seed. For manual harvesting methods in which the dried, shocked sesame is moved to a threshing floor or over a plastic or cloth, preferred plant varieties include dehiscent, or super shattering, in which less than 10% of the seeds set are retained in the capsule.

Other methods involve leaving the shocks in the fields, and when the shocks are dry, the sesame is turned upside down and struck with an implement to shake out all of the seed. For this type of manual harvesting method, it is preferred that plant varieties rated as "shattering" be used, wherein the capsule retains as much of the sesame seed as possible until the farmer inverts the stalk. Common methods of manual harvest are discussed in Weiss, E. A. "Sesame", *Oilseed crops* (2$^{nd}$ ed.), Chapter 5, Blackwell Science, Inc., Malden, Mass., p. 131-164 (2000).

In an effort to mechanize the harvest of sesame, D. G. Langham introduced the use of binders in Venezuela in 1944. The binders were used to cut and bundle the sesame plants, manual labor was used to shock the cut plants, and combines were brought in to thresh the shocks. This methodology is still used in Venezuela and Paraguay and is considered "semimechanized harvest" because it still requires some manual labor. It was determined that seed shattering during mechanized harvesting methods caused considerable loss of sesame seed. While mechanization was considered to be essential for crop production in the Western hemisphere, the dehiscence of the sesame seed capsule was the principal obstacle to the widespread acceptance of sesame as a commercial crop. (Langham, D. G. 1949. "Improvement of Sesame in Venezuela," *Proceedings First International Sesame Conference*, Clemson Agricultural College, Clemson, S.C., pp. 74-79). As programs to introduce sesame production in the United States in Arizona, South Carolina, Nebraska, Oklahoma, and Texas were initiated, mechanization was considered essential due to high labor costs. Kalton, one of the Texas researchers, reported that the shattering nature of available strains was the main obstacle in complete mechanization of the sesame crop. (Kalton, R. 1949. "Sesame, a promising new oilseed crop for Texas," *Proc First International Sesame Conference*, Clemson Agricultural College, Clemson, S.C., pp. 62-66).

In 1943, D. G. Langham found a mutation on a sesame plant. Capsules did not open on plants expressing this mutation. In succeeding generations, Langham showed that it was a recessive single gene which produced this indehiscence, where all the seeds were retained inside the unopened capsule. While it was believed that indehiscence would solve the problem of seed loss on mechanized harvesting, it was found that the capsules were too tough to effectively release the seed. Many of the capsules passed through a combine without opening. When more rigorous combining was attempted, an increase in efficiency of capsule opening was achieved but at the expense of seed quality. Seeds were broken due to the more rigorous combine conditions, and the broken seeds released free fatty acids. Chemical reactions with free fatty acids led to rancidity and concomitant undesirability of the harvested seed.

The indehiscent sesame varieties described above were used by various plant breeders in an attempt to develop desirable sesame lines. In addition to traditional cross-breeding approaches, some attempted to alter the chromosome numbers through tetraploids and interspecific crosses. Yermanos attempted to improve release of seed by increasing the length of the capsule so that there would be more surface for the combine to crack the capsules open (personal communication). Unfortunately, even with a small opening on the top of the capsule, a high percentage of broken seed was found on mechanized harvesting, preventing commercial use of this sesame line.

D. G. Langham reported in the late 1950's that the placenta attachment between each sesame seed and the placenta was important in the retention of seed in the capsule. He believed that he could improve the shatter resistance of sesame with increased placenta attachment but did not believe that all the seed could be retained in the capsule (Langham, D. G., Rodriguez, Maximo, and Reveron Esteban. 1956. "Dehiscencia y otras caracteristícas del ajonjoli, *Sesamum indicum* L., en relación con el problema de la cosecha", Genesa, Maracay, Venezuela, pp. 3-16). However, Yermanos reported that during capsule maturity, the placenta attachment gradually weakens and is obliterated when the capsule is completely desiccated. (Yermanos, D. M. 1980. "Sesame. Hybridization of crop plants," *Am Soc Agronomy-Crop Sci of America*, pp. 549-563). Thus, it appeared that the placenta attachment would have little effect on seed retention in dry, mature capsules during harvesting. A seamless gene which retained all the seed in the capsules was discovered by D. G. Langham and D. R. Langham in 1986. (Langham, D. R., "Shatter resistance in sesame", In: L. Van Zanten (ed.), Sesame improvements by induced mutations, *Proc. Final FAO/IAEA Co-ord. Res. Mtng.*, IAEA, Vienna, TECDOC-1195, p. 51-61 (2001)). This was crossed with shattering types, and some progeny had an opening at the tip of the capsule. The seamless capsules were similar to the indehiscent capsules in that it was too difficult to remove the seed from the capsule without damaging the seed.

In 1982, the first non-shattering line (retaining 50-70% of the seeds set) requiring no manual labor was introduced. This line could be harvested by swathing the sesame, leaving it to dry in the field, and then picking it up by a combine. This methodology is fully mechanized, but it is rarely used because it uses two machines—one to swath and the other to combine. Although complete mechanization was achieved, extensive loss of seed due to adverse weather conditions continued to occur. (Langham, D. R., 2001, supra).

Other varieties were developed between 1988 and 1997 which allowed for direct combining which is the fully mechanized methodology that is currently used in the United States because it only requires one machine. With these varieties there was 70-90% seed retention, but extensive loss of seed due to environmental factors such as wind and rain continued to occur. Lines that generally yielded 80% of the seed under ideal conditions would yield only 45-65% under adverse conditions. Thus, while many of the crosses began to moderate the deleterious effects of mechanized harvesting, none were able to increase the yields to the level of manually harvesting shattering cultivars.

A breakthrough was accomplished when non-dehiscent (ND) sesame was developed and patented by Derald Ray Langham. ND sesame was found to possess the proper characteristics which would enable mechanical harvesting without the seed loss disadvantages reported with prior varieties.

U.S. Pat. No. 6,100,452 which issued Aug. 8, 2000, disclosed a method for sesame breeding which resulted in non-dehiscent (ND) sesame lines. Sesaco 22 (S22), Sesaco 23 (S23), Sesaco 24 (S24), 19A, and 11W, representative seed having been deposited under ATCC accession number PTA-1400, PTA-1401, PTA-1402, PTA-1399, and PTA-1398, respectively were examples of ND sesame lines which were made according to the claimed method. These sesame lines are characterized by their high degree of seed retention within the capsule despite adverse weather conditions such as wind and rain and the retention of a sufficient amount of sesame seed during mechanized harvesting to be competitive with manual harvesting with minimization of seed breakage.

U.S. Pat. No. 6,815,576 which issued Nov. 9, 2004, disclosed a non-dehiscent sesame cultivar S25, representative seed having been deposited under ATCC accession number PTA-4258. S25 is a stable, commercially suitable sesame line providing an early maturity cycle which extends the planting region to more northern latitudes and improved resistance against common fungal diseases.

U.S. Pat. No. 6,781,031 which issued Aug. 24, 2004, disclosed a non-dehiscent sesame cultivar S26, representative seed having been deposited under ATCC accession number PTA-4317. S26 is a stable, commercially suitable sesame line providing improved drought resistance, improved resistance against common fungal diseases, a larger seed, and a later maturity cycle which limits the planting region to more southern latitudes.

U.S. Pat. No. 7,148,403 which issued Dec. 12, 2006, disclosed a non-dehiscent sesame cultivar S28, representative seed having been deposited under ATCC accession number PTA-6008. S28 is a stable, commercially suitable sesame line providing improved resistance against common fungal diseases, a comparably large seed, and an early maturity cycle which extends the planting region to more northern latitudes.

U.S. Pat. No. 7,332,652 which issued Feb. 19, 2008, disclosed a non-dehiscent sesame cultivar S29, representative seed having been deposited under ATCC accession number PTA-6598. S29 is a stable, commercially suitable sesame line providing improved resistance against common fungal diseases, improved yields, and an early maturity cycle which extends the planting region to more northern latitudes.

Herein disclosed is a sesame variety designated Sesaco 32 (S32), which exhibits Improved Non-Dehiscence, a new category of non-dehiscence.

SUMMARY OF THE INVENTION

In one aspect, the invention comprises a seed of sesame variety designated Sesaco 32 (S32), a sample of said seed having been deposited under ATCC Accession No. PTA-8888.

In another aspect, the invention comprises a sesame plant produced by growing the seed of sesame variety S32, a sample of said seed having been deposited under ATCC Accession No. PTA-8888.

In yet another aspect, the invention comprises plant cells derived from a sesame plant, said plant produced by growing the seed of sesame variety S32, a sample of said seed having been deposited under ATCC Accession No. PTA-8888. The plant cells may be selected, for example, from pollen, tissue culture of regenerable cells, and asexually reproducing cultivars.

In yet another aspect, the invention comprises a sesame plant having all the physiological and morphological characteristics of sesame variety S32, a sample of the seed of said variety having been deposited under ATCC Accession No. PTA-8888.

In another aspect, the invention comprises a sesame plant regenerated from a tissue culture of regenerable cells produced from plant cells derived from sesame variety S32, a sample of said seed having been deposited under ATCC Accession No. PTA-8888, wherein said regenerated sesame plant has all the physiological and morphological characteristics of said sesame variety S32. The plant cells may be derived from S32 seeds or plant cells from tissue from a sesame plant produced by growing the seed of sesame variety S32.

In another aspect, the invention comprises a method of producing sesame seed, comprising crossing a first parent sesame plant with a second parent sesame plant and harvesting the resultant sesame seed, wherein said first or second parent sesame plant was produced by growing seed of sesame variety S32, a sample of said seed having been deposited under ATCC Accession No. PTA-8888.

BRIEF DESCRIPTION OF THE DRAWINGS

FIG. 1 depicts the lineage of S32.

DETAILED DESCRIPTION

Figure 2:
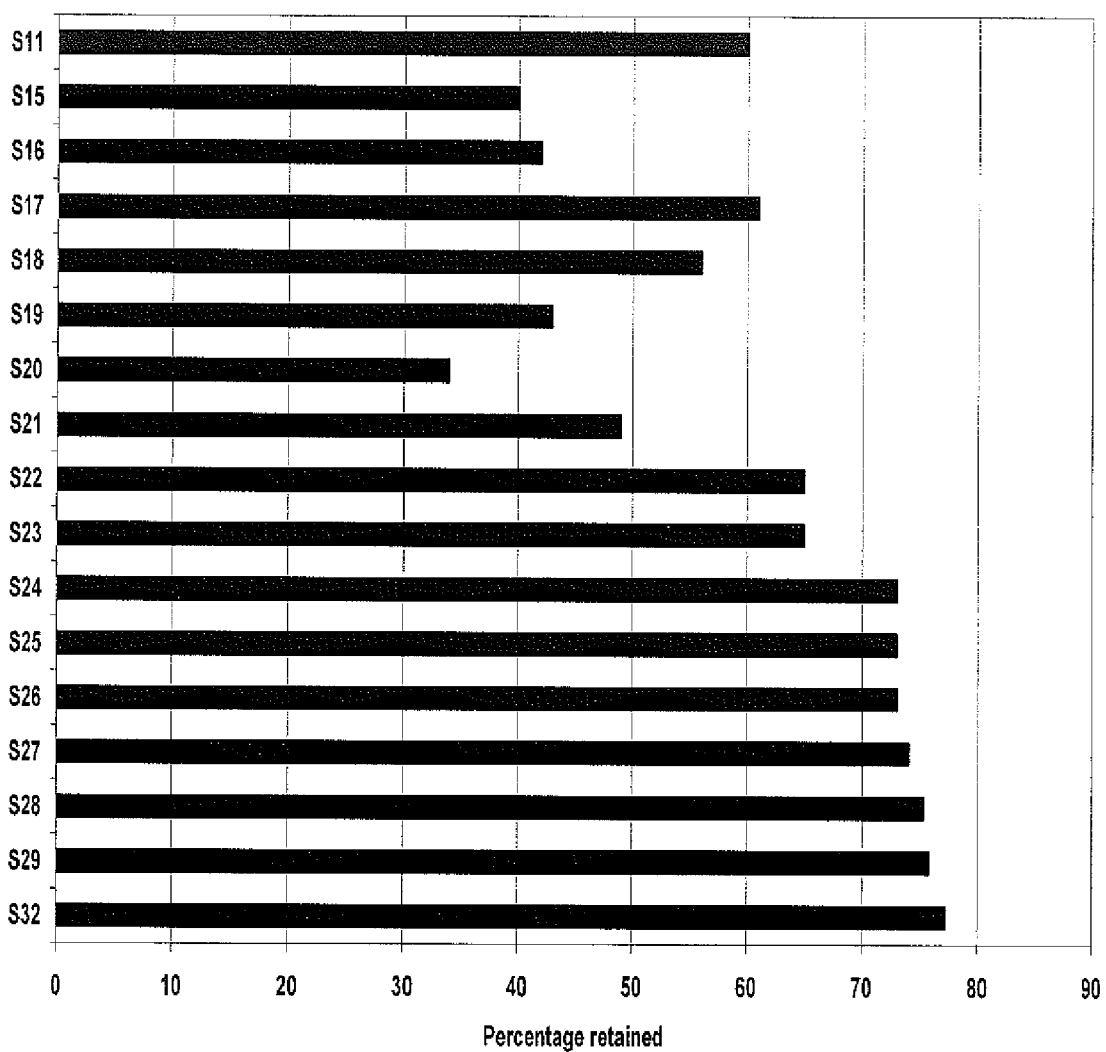
FIG. 2 depicts a comparison of the percent of seed retention during in shaker shatter resistance testing from 1997 to 2006 for sesame varieties released by Sesaco that have been used in direct harvest: Sesaco 11 (S11) released in 1988-1996, Sesaco 15 (S15) released in 1991, Sesaco 16 (S16) released in 1992-1996, Sesaco 17 (S17) released in 1994-2000, Sesaco 18 (S18) released in 1994-1996, Sesaco 19 (S19) released in 1994-1995, Sesaco 20 (S20) released in 1995-1997, Sesaco 21 (S21) released in 1995-2001, Sesaco 22 (S22) released in 1997-1999, Sesaco 23 (S23) released in 1998-2000, Sesaco 24 (S24) released in 1998-2004, Sesaco 25 (S25) released in 2001-2008, Sesaco 26 (S26) released in 2002-2008, Sesaco 28 (S28) released in 2004-2008, Sesaco 29 (S29) released in 2005-2008, and Sesaco 32.

Sesame plants have been studied for their response to seasonal and climatic changes and the environment in which they live during the different phases and stages of growth and development. This type of study, called "phenology" has been documented by the inventor in Langham, D. R. 2007. "Phenology of sesame," In: J. Janick and A. Whipkey (ed.), *Issues in New Crops and New Uses*, ASHS Press, Alexandria, Va.

Table I summarizes the phases and stages of sesame, and will be useful in describing the present invention.

TABLE I

Phases and stages of sesame

| Stage/Phase | Abbreviation | End point of stage | DAP$^z$ | No. weeks |
|---|---|---|---|---|
| Vegetative | VG | | | |
| Germination | GR | Emergence | 0-5 | 1– |
| Seedling | SD | 3$^{rd}$ pair true leaf length = 2$^{nd}$ | 6-25 | 3– |
| Juvenile | JV | First buds | 26-37 | 1+ |
| Pre-reproductive | PP | 50% open flowers | 38-44 | 1– |
| Reproductive | RP | | | |
| Early bloom | EB | 5 node pairs of capsules | 45-52 | 1 |
| Mid bloom | MB | Branches/minor plants stop flowering | 53-81 | 4 |
| Late bloom | LB | 90% of plants with no open flowers | 82-90 | 1+ |
| Ripening | RI | Physiological maturity (PM) | 91-106 | 2+ |
| Drying | DR | | | |
| Full maturity | FM | All seed mature | 107-112 | 1– |
| Initial drydown | ID | 1$^{st}$ dry capsules | 113-126 | 2 |
| Late drydown | LD | Full drydown | 127-146 | 3 |

$^z$DAP = days after planting. These numbers are based on S26 in 2004 Uvalde, Texas, under irrigation.

There are several concepts and terms that are used in this document that should be defined. In the initial drydown stage in Table I, the capsules begin to dry and open. This stage ends when 10% of the plants have one or more dry capsules. The late drydown stage ends when the plants are dry enough so that upon harvest, the seed has a moisture of 6% or less. At this point some of the capsules have been dry for 5 weeks in the example used in Table I, but in other environments for other varieties, the drying can stretch to 7 weeks. The "ideal harvest time" is at the end of the late drying stage. At this point, a combine (also sometimes referred to as a combine harvester, a machine that combines the tasks of harvesting, threshing, and cleaning grain crops) can be used to cut and thresh the plants and separate the seed from the undesired plant material. However, at times, weather may prevent harvest at the ideal time. The plants may have to remain in the field for as much as an additional four weeks, and in some cases even longer. Thus, time $t_0$ corresponds to the ideal harvest time and time $t_1$, which corresponds to the time the grower actually harvests the sesame is a time later than time $t_0$.

Sesame cultivar Sesaco 32 (hereinafter "S32") is a variety which exhibits Improved Non-Dehiscence (IND) characteristics and desirable characteristics which make it a commercially suitable sesame line. IND characteristics are defined in comparison to non-dehiscence (ND) characteristics first described and defined by the inventor in U.S. Pat. No. 6,100,452. Compared to ND sesame, IND sesame has more seed in the capsules when measured between 4 and 9 weeks after the ideal harvest time.

Without wishing to be bound by one particular theory, it is believed that this increased amount of seed in the capsules is may be due to the S32 variety having the ability to better withstand adverse environmental conditions such as inclement or harsh weather. Examples of adverse weather conditions as to which S32 has been subjected to in this regard are rain, fog, dew, and wind.

Concurrently filed and commonly owned U.S. patent application Ser. No. 12/041,257, filed Mar. 3, 2008, is herein incorporated by reference as if fully set forth herein. This application discloses Improved Non-Dehiscent Sesame and the present invention. S32 is an example of a variety which resulted from breeding methods described therein.

S32 exhibits improved shatter resistance, acceptable resistance to common fungal diseases, and a maturity that allows a wide geographical range. Further, S32 exhibits higher yield in geographical locations desirable for sesame planting, and exhibits desirable seed size and seed color. S32 is suitable for planting in areas that have approximately a 21° C. ground temperature when planted in the spring and night temperatures above 5° C. for normal termination. An exemplary desirable geographical area for S32 is from South Texas at the Rio Grande to southern Kansas and from east Texas westward to elevations below 1,000 meters. S32 also has performed well in California, New Mexico, and Arizona.

Other exemplary areas are areas of the United States or of the world which areas have similar climatic conditions and elevations.

The pedigree method of plant breeding was used to develop S32. Sesame is generally self-pollinated. Crossing is done using standard techniques as delineated in Yermanos, D. M. 1980. "Sesame. Hybridization of crop plants," *Am Soc Agronomy-Crop Sci of America*, pp. 549-563 and U.S. Pat. No. 6,100,452. Ashri provides an overview of sesame breeding in Ashri, A. (1998). "Sesame breeding," *Plant Breed. Rev.* 16:179-228 and Ashri, A. 2007. Sesame (*Sesamum indicum* L.). In: R. J. Singh, Ed., Genetic Resources, Chromosome Engineering, and Crop Improvement, Vol. 4, Oilseed Crops, p. 231-289, CRC Press, Boca Raton, Fla., USA The lineage of S32 is presented in FIG. 1. G8 (1) was a line obtained from D. G. Langham in 1977 and first planted by Sesaco in the Kamman nursery (Wellton, Ariz.) in 1978. It was a selection from the cultivar 'Guacara' which D. G. Langham developed in Venezuela in the 1950s. Guacara was an initial selection from a cross that later produced one of the major varieties in Venezuela—Aceitera. Within Sesaco, G8 first carried the identifier X011 and was later changed to TG8.

111 (2) was a line obtained from the NPGS (PI173955) in 1979 and first planted by Sesaco in the Woods nursery (Wellton, Ariz.) in 1981. NPGS obtained it in 1949 from W. N. Koelz, USDA, Beltsville, Md. who obtained it from India.

Within Sesaco, 111 first carried the identifier 0858 and was then changed to X11. In 1985, a selection of this line became Sesaco 4 (S04).

191 (3) was a selection from 192 which was a line obtained from the M. L. Kinman in 1980 and first planted by Sesaco in the Woods nursery (Wellton, Ariz.) in 1981. The line was originally T61429-B-4-1-3 from the Kinman USDA sesame program, College Station, Tex., which had been in cold storage at Ft. Collins, Colo. In 1997, the line was transferred to the NPGS, Griffin, Georgia and given the identifier PI599462. Within Sesaco, 192 first carried the identifier 1479 and then was changed to X191 and X193. In 1985, a selection from X193 became Sesaco 3 (S03) and a selection of X191 became Sesaco 7 (S07).

MEL (4) was a line obtained from Mel Tiezen in 1978 and first planted by Sesaco in the Kamman nursery (Wellton, Ariz.) in 1978. Mr. Tiezen obtained it from a farmer in Mexico. Within Sesaco, MEL first carried the identifier 0543 and was then changed to TMEL.

G54 (5) was a line obtained from the Sesamum Foundation (D. G. Langham, Fallbrook, Calif.) in 1977 and first planted in the Kamman nursery (Wellton, Ariz.) in 1978. It was obtained with the designator SF408. The Sesamum Foundation obtained it from John Martin in 1962. This line was given to Mr. Martin by D. G. Langham. G54 was a selection from G53.48, a cross made by D. G. Langham in 1954 in Guacara, Venezuela. Within Sesaco, G54 carried the identifier 0408 and was then changed to TG54.

193 (6) was a selection from 192 which was a line obtained from the M. L. Kinman in 1980 and first planted by Sesaco in the Woods nursery (Wellton, Ariz.) in 1981. The line was originally T61429-B-4-1-3 from the Kinman USDA sesame program, College Station, Tex., which had been in cold storage at Ft. Collins, Colo. In 1997, the line was transferred to the NPGS, Griffin, Ga. and given the identifier PI599462. Within Sesaco, 192 first carried the identifier 1479 and then was changed to X191 and X193. In 1985, a selection from X193 became Sesaco 3 (S03) and a selection of X191 became Sesaco 7 (S07).

104 (7) was a line obtained from the Sesamum Foundation (D. G. Langham, Fallbrook, Calif.) in 1977 and first planted in the Kamman nursery (Wellton, Ariz.) in 1978. It was obtained with the designator SF084. The Sesamum Foundation obtained it from Maximo Rodriguez in 1961. He had collected it from Mexico where it was known as Instituto 8. Instituto 8 was a selection from G53.48, a cross made by D. G. Langham in 1953 in Guacara, Venezuela. Within Sesaco, 104 carried the identifier 0084. In 1983, a selection of this line became Sesaco 2 (S02).

192 (8) was a line obtained from the M. L. Kinman in 1980 and first planted by Sesaco in the Woods nursery (Wellton, Ariz.) in 1981. The line was originally T61429-B-4-1-3 from the Kinman USDA sesame program, College Station, Tex., which had been in cold storage at Ft. Collins, Colo. In 1997, the line was transferred to the NPGS, Griffin, Georgia and given the identifier PI599462. Within Sesaco, 192 first carried the identifier 1479 and then was changed to X191 and X193. In 1985, a selection from X193 became Sesaco 3 (S03) and a selection of X191 became Sesaco 7 (S07).

118 (9) was a line obtained from the NGPS (PI425944) in 1979 and first planted in Kamman nursery (Wellton, Ariz.) in 1979. The NGPS obtained it in 1978 from P. F. Knowles, University of California, Davis, Calif., who collected it in Pakistan. Within Sesaco, it carried the identifier 1118 and then changed to X118 and then to T118.

700 (10) was a line obtained from the NGPS (PI292144) in 1979 and first planted by Sesaco in the Woods nursery (Wellton, Ariz.) in 1981. NPGS obtained it in 1963 from Hybritech Seed International, a unit of Monsanto, U.S., which obtained it from Israel. In viewing this material in 1986, A. Ashri of Israel concluded that it was an introduction to Israel. The material is similar to introductions from India and Pakistan. Within Sesaco, 700 first carried the identifier 0700 and was later changed to T700.

702 (11) was a line obtained from the NGPS (PI292146) in 1979 and first planted in Woods nursery (Wellton, Ariz.) in 1981. The NGPS obtained it in 1963 from Hybritech Seed International, a unit of Monsanto, U.S., which obtained it from Israel. In viewing this material in 1986, A. Ashri of Israel concluded that it was an introduction to Israel. The material is similar to introductions from the Indian subcontinent. Within Sesaco, it has carried the identifier 0702 and then changed to X702 and then to X702C. In 1986, a selection from X702C became Sesaco 12 (S12).

111X (12) was an outcross in the 111 (2) plot BT0458 in the Nickerson nursery (Yuma, Ariz.) in 1982. Within Sesaco, it carried the identifier E0745 and later changed to T111X.

96B (13) was an outcross in the 191 (3) in plot 4637 in the McElhaney nursery (Wellton, Ariz.) in 1983. Within Sesaco, it carried the identifier E0690 which later became X196B and was later changed to T96B.

B043 (14) was a cross made by Sesaco between G8 (1) and MEL (4) in the Kamman nursery (Yuma, Ariz.) in 1978. Within Sesaco, it carried the identifier B043.

F853 (15) was a cross made by Sesaco between 104 (15) and 192 (8) in the Nickerson nursery (Yuma, Ariz.) in 1982. Within Sesaco, it carried the identifier F853.

F822 (16) was a cross made by Sesaco between 111 (2) and 192 (8) in the Nickerson nursery (Yuma, Ariz.) in 1982. Within Sesaco, it carried the identifier F822.

804 (17) was a cross made by Sesaco between G8 (1) and 111X (12) in the Nickerson nursery (Yuma, Ariz.) in 1982. Within Sesaco, it has carried the identifier F804; in 1988, a selection of this line became Sesaco 11 (S11).

S11 (18) was a cross made by Sesaco between G8 (1) and 111X (12) in the Nickerson nursery (Yuma, Ariz.) in 1982. Within Sesaco, it has carried the identifier F804; in 1988, a selection of this line became Sesaco 11 (S11).

C063 (19) was a cross made by Sesaco between B043 (14) and G54 (5) in the Kamman nursery (Yuma, Ariz.) in 1979. Within Sesaco, it carried the identifier C063.

F820 (20) was a cross made by Sesaco between 111X (12) and 104 (7) in the Nickerson nursery (Yuma, Ariz.) in 1982. Within Sesaco, it carried the identifier F820.

562 (21) was a cross made by Sesaco between F822 (16) and 700 (10) in the McElhaney nursery (Wellton, Ariz.) in 1983. Within Sesaco, it first carried the identifier G8562 and was later changed to T562.

K0338 (22) was a cross made by Sesaco between 804 (17) and 96B (13) in the Hancock nursery (Wellton, Ariz.) in 1986. Within Sesaco, it carried the identifier K0338.

233 (23) was a cross made by Sesaco between C063 (19) and 193 (6) in the Hancock nursery (Weilton, Ariz.) in 1984. Within Sesaco, it first carried the identifier H6233 and was later changed to T233.

578 (24) was a cross made by Sesaco between F820 (20) and F853 (15) in the McElhaney nursery (Weliton, Ariz.) in 1983. Within Sesaco, it first carried the identifier G8578 and was later changed to T578.

56B (25) was a cross made by Sesaco between 804 (17) and 562 (21) in the Wright nursery (Tacna, Ariz.) in 1987. Within Sesaco, it first carried the identifier KAN00 and was later changed to X56B and then to TS6B.

L6651 (26) was a cross made by Sesaco between 72C (11) and 804 (17) in the Wright nursery (Tacna, Ariz.) in 1987. Within Sesaco, it carried the identifier L6651.

ZSA (27) was a cross made by Sesaco between K0338 (22) and S11 (18) in the Yuma greenhouse (Yuma, Ariz.) in 1986. Within Sesaco, it first carried the identifier KAC22 and was later changed to XZSA and then to TZSA.

031 (28) was a cross made by Sesaco between 578 (24) and 118 (9) in the Ramsey nursery (Roll, Ariz.) in 1984. Within Sesaco, it carried the identifier H0031 and then changed to T031.

2CA (29) was a cross made by Sesaco between L6651 (26) and S11 (18) in the Wright nursery (Roll, Ariz.) in 1988. Within Sesaco, it has carried the identifier LCX02 and later changed to X2CA and then to T2CA.

SAA (30) was a cross made by Sesaco between ZSA (27) and 233 (23) in the Sharp nursery (Roll, Ariz.) in 1989. Within Sesaco, it has carried the identifier PE046 and later changed to XSAA and then to TSM.

2CB (3) was a cross made by Sesaco between 56B (25) and 2CA (29) in the Gilleland nursery (Uvalde, Tex.) in 1992. Within Sesaco, it has carried the identifier AG729 and later changed to X2CB and then to T2CB.

13H (32) was a cross made by Sesaco between SM (27) and 031 (28) in the Gilleland nursery (Uvalde, Tex.) in 1994. Within Sesaco, it has carried the identifier CM413 and later changed to X13H and then to T13H.

S32 (33) was obtained with the following method. A cross between 13H (32) and 2CB (31) was made in Year 1 (hereinafter "Year" is abbreviated as "YR") and designated GD038.

The resulting seed (D038) was planted in a greenhouse in YR1-YR2.

The seed from this plant (E365) was planted in a plot (7105) in YR2. Eight individual plants were selected based on having a capsule zone much longer than the 13H parent, and the line was segregating capsule length.

The seed (7503) from one of the plants was planted in a plot (4477) in YR3. Twelve individual plants were selected based on very good drought resistance, numerous capsules, and seed very close to the top.

The designator was changed to X3HD. The seed (2642) from one of the plants was planted in plot 8071 in YR4. Two individual plants were harvested based on having a low first capsule, even though they did not exhibit high yield.

The seed from a shaker shatter resistance test as disclosed in U.S. Pat. No. 6,100,452 of the 2 individuals (R2151) was planted in YR5. The test plot was accessed by deer which destroyed much of it, but two individual plants survived and were used for further work.

The seed (4651) from one of the plants was planted in plot 0054 in YR6. Two plants were selected based on a good capsule gap, even after being subjected to hurricane-force winds, numerous capsules and good kill resistance.

The seed (4282) from one of the plants were planted in buffer plot WH47 in YR7. A bulk of 75 plants was selected based on having good yield in the Lubbock, Tex. area, numerous capsules, good lodging and shatter resistance when tested in late December. Commercially, plots would have been harvested in early October.

The seed (0621) was planted in strip VE77n in YR8. Most of the plants were selected for a commercial testing.

The seed (3HDGW) was tested in YR9 under farm conditions. The field was combined and this seed designated as S32.

Along with breeding programs, tissue culture of sesame is currently being practiced in such areas of the world as Korea, Japan, China, India, Sri Lanka and the United States. One of ordinary skill in the art may utilize sesame plants grown from tissue culture as parental lines in the production of non-dehiscent sesame. Further IND sesame may be propagated through tissue culture methods. By means well known in the art, sesame plants can be regenerated from tissue culture having all the physiological and morphological characteristics of the source plant.

The present invention includes the seed of sesame variety S32 deposited under ATCC Accession No. PTA-8888; a sesame plant or parts thereof produced by growing the seed deposited under ATCC Accession No. PTA-8888; any sesame plant having all the physiological and morphological characteristics of sesame variety S32; any sesame plant all the physiological and morphological characteristics of a sesame plant produced by growing the seed deposited under ATCC Accession No. PTA-8888. The present invention also includes a tissue culture of regenerable cells produced from the seed having been deposited under ATCC Accession No. PTA-8888 or a tissue culture of regenerable cells from sesame variety S32 or a part thereof produced by growing the seed of sesame variety S32 having been deposited under ATCC Accession No. PTA-8888. A sesame plant regenerated from a tissue culture of regenerable cells produced from the seed having been deposited under ATCC Accession No. PTA-8888 or from sesame variety S32, wherein the regenerated sesame plant has all the physiological and morphological characteristics of sesame variety S32 is also contemplated by the present invention. Methods of producing sesame seed, comprising crossing a first parent sesame plant with a second parent sesame plant, wherein the first or second parent sesame plant was produced by seed having been deposited under ATCC Patent Deposit Designation No. PTA-8888 is part of the present invention.

Unless otherwise stated, as used herein, the term plant includes plant cells, plant protoplasts, plant cell tissue cultures from which sesame plants can be regenerated, plant calli, plant clumps, plant cells that are intact in plants, or parts of plants, such as embryos, pollen, ovules, flowers, capsules, stems, leaves, seeds, roots, root tips, and the like. Further, unless otherwise stated, as used herein, the term progeny includes plants derived from plant cells, plant protoplasts, plant cell tissue cultures from which sesame plants can be regenerated, plant calli, plant clumps, plant cells that are intact in plants, or parts of plants, such as embryos, pollen, ovules, flowers, capsules, stems, leaves, seeds, roots, root tips, and the like.

Sesame cultivar S32 has been tested experimentally over several years under various growing conditions ranging from South Texas to Northern Oklahoma. Sesame cultivar S32 has shown uniformity and stability within the limits of environmental influence for the characters listed in Table II below. Table II provides the name, definition, and rating scale of each character as well as the method by which the character is measured. Under the rating section, the rating for S32 is presented in bold text. Additionally, the distribution of the character in Sesaco's sesame development program is indicated under the rating section. Sesaco uses slightly different character specifications from "Descriptors for sesame", AGP: IBPGR/80/71, IBPGR Secretariat, Rome, (1981) and from the form "Sesame (*Sesamum indicum*)", U.S. Department of Agriculture Plant Variety Protection Office, Beltsville, Md. The descriptors in those documents were developed in the early 1980s and have not been updated to incorporate new concepts in sesame data collection.

Table II provides characteristics of S32 for forty-three (43) traits. Numerical ratings and values reported in this table were experimentally determined for S32 with prior sesame varieties in side by side replicated trials. Actual numerical values and ratings for a given variety will vary according to the environment, and the values and ratings provided in Table II were obtained in the environment specified in the parenthetical following the S32 rating. Table V provides a direct comparison between the new S32 variety and the prior varieties thus demonstrating the relative differences between the varieties in the side by side trials.

TABLE II

Characters Distinguishing the S32 Line

| Character | Rating | Methodology |
| --- | --- | --- |
| (1) BRANCHING STYLE<br>The potential amount of true branching in a line | S32 = B<br>(All crops, all nurseries)<br>Subjective rating based on the following values:<br>U = Uniculm - no branching except weak branches in open<br>B = True branches<br>Distribution within Sesaco based on stable lines in the crossing program in 1982-2001 (Total number of samples tested = 1,333)<br>U = 42.4%<br>B = 57.6% | The amount of branching on any particular plant depends on the space around the plant. In high populations, branching can be suppressed. This rating should be based on potential as expressed on end plants and plants in the open. True branches start in the leaf axil below the first flower, and they begin to emerge before the first open flower. As long as there is light into the leaf axils, there will be additional branches that start below the first branches in subsequently lower nodes. Weak branches occur when a plant is in the open. They develop in the lowest nodes and subsequent branches start at higher nodes. There are lines that will not branch in any circumstance. Some lines in the open will put on spontaneous branches late in the cycle. True and weak branches do not have a capsule in the same leaf axil, whereas the spontaneous branches form under the capsule after the capsule has formed. Spontaneous branches are not counted as branches. There are rare lines where the flowering pattern is to put on flowers on lower nodes late in the cycle. In this case, the capsule is formed after the branch is developed. This pattern should not be termed spontaneous branching, and the branch is normally counted as a true branch. There are branched lines that have secondary branches on the branches. In a few cases, there can be tertiary branches. Additional branches generally appear in low populations.<br>COMMENTS: the effects of light appear to have more of an effect on branching than moisture and fertility. High populations suppress branching. |
| (2) NUMBER OF CAPSULES PER LEAF AXIL<br>The predominant number of capsules per leaf axil in the middle half of the capsule zone | S32 = 1<br>(All crops, all nurseries)<br>Subjective rating based on the following values:<br>1 = Single<br>3 = Triple<br>Based on potential as described in the methodology presented herein<br>Distribution within Sesaco based on stable lines in the crossing program in 1982-2001 (Total number of samples tested = 1,327)<br>1 = 58.3%<br>3 = 41.7% | Rating can be taken from about 60 days after planting through to the end of the crop.<br>NUMBER OF CAPSULES PER LEAF AXIL is highly dependent on moisture, fertility, and light. In triple capsule lines, the central capsule forms first, and axillary capsules follow a few days later. Triple capsule lines have the potential to put on axillaries, but will not do so if plants do not have adequate moisture and/or fertility. In drought conditions, some triple capsule lines will produce only a central capsule for many nodes. In these lines, when there is adequate moisture through rain or irrigation, some will add axillary capsules on only new nodes, while others will add axillary capsules to all nodes. Some triple capsule lines will not put on axillary capsules if there is no direct sunlight on the leaf axil. To date, lines with single capsules have nectaries next to the central capsule in the middle of the capsule zone while triple capsules do not. However, some lines have what appear to be nectaries on the lower capsules of triple lines, but upon close examination, they are buds which may or may not eventually develop |

TABLE II-continued

Characters Distinguishing the S32 Line

| Character | Rating | Methodology |
|---|---|---|
| | | into a flower and then a capsule. In most triple capsule lines, the lower and upper nodes have single capsules. There are some lines where the end plants can put on 5 capsules/leaf axil and a few that have the potential to put on 7 capsules/leaf axil. 5 and 7 capsules only appear with open plants with high moisture and fertility. In some environments, single capsule lines will put on multiple capsules on 1 node and rarely on up to 5 nodes. These lines are not considered triple capsule lines. |
| (3) MATURITY CLASS The maturity of a line in relation to a standard line. Currently, the standard line is S26 at 100 days | S32 = M for 97days (Uvalde nursery[a,] 2005-2007) Subjective rating based on the following values: V = Very early (<85 days) E = Early (85-94 days) M = Medium (95-104 days) L = Late (105-114 days) T = Very late (>114 days) Distribution within Sesaco based on stable lines in the crossing program in 1998-2001 (Total number of samples tested = 650) V = 1.2% E = 26.8% M = 56.2% L = 12.9% T = 2.9% | The basis for this data point is DAYS TO PHYSIOLOGICAL MATURITY (Character No. 29). S24 is the standard line to be used to compute MATURITY CLASS. In 1998-2001, the maturity of S24 averaged 95 days in the Uvalde, TX, nursery. Through 2006, the standard was adjusted using S24. As S24 was phased out of commercial planting, a new standard needed to be established, and S26 was selected. In 2001-2006 S26 averaged 5 days longer than S24. For each line, the physiological maturity for each year is subtracted by the S26 maturity for that year in that nursery, and then the number of days of difference is averaged. The average is then added to 100. See DAYS TO PHYSIOLOGICAL MATURITY (Character No. 29) for the effects of the environment on MATURITY CLASS. |
| (4) PLANT PHENOTYPE A three character designation that provides the branching style, number of capsules per leaf axil, and the maturity class | S32 = B1M (All crops; all nurseries) Subjective rating based on the following values: BRANCHING STYLE U = Uniculm - no branching except weak branches in open B = True branches NUMBER OF CAPSULES PER LEAF AXIL 1 = Single 3 = Triple MATURITY CLASS V = Very early (<85 days) E = Early (85-94 days) M = Medium (96-104 days) L = Late (105-114 days) T = Very late (>114 days) Distribution within Sesaco based on stable lines in the crossing program in 1998-2001 (Total number of samples tested = 650) U1V = 0% U3V = 1.1% U1E = 3.8% U3E = 8.3% U1M = 16.0% U3M = 12.0% U1L = 3.4% U3L = 2.2% U1T = 0.5% U3T = 0.6% B1V = 0% B3V = 0.2% B1E = 8.0% B3E = 6.3% B1M = 23.2% B3M = 4.8% B1L = 6.5% B3L = 1.0% B1T = 1.6% B3T = 0.4% | The first character is the BRANCHING STYLE (Character No. 1), followed by the NUMBER OF CAPSULES PER LEAF AXIL (Character No. 2), and then the MATURITY CLASS (Character No. 3). When these characters are placed in a matrix, there are 20 potential phenotypes. The phenotype provides an overview of the general appearance of the plant. There is a very high correlation between MATURITY CLASS and HEIGHT OF PLANT (Character No. 5). |
| (5) HEIGHT OF PLANT The height of the plant from the ground to the top of the highest capsule with viable seed | S32 = 147 cm (Uvalde nursery, 2007) Value based on an the average of a minimum of three plants (unit of measure: cm) | The measurement is made after the plants stop flowering. For plants that are not erect or have lodged, the plant should be picked up for the measurement. In most lines the highest capsule is on the main stem. In lines with the dt/dt alleles |

TABLE II-continued

Characters Distinguishing the S32 Line

| Character | Rating | Methodology |
|---|---|---|
| | Distribution within Sesaco based on stable lines in the crossing program in 1999-2001 (Total number of samples tested = 2274) low = 56 cm; high = 249 cm<br>1 = <94.6 cm; 5.2%<br>2 = <133.2 cm; 34.6%<br>3 = <171.8 cm; 54.9%<br>4 = <210.4 cm; 5.1%<br>5 = >210.3 cm; 0.1%<br>avg. = 134.8 cm, std = 23.5 | (determinate), the highest capsule is on the branches.<br>COMMENTS: this height is dependent on the amount of moisture, heat, fertility, and population. Increased values generally increase the height. In a high population, the height will only increase if there is adequate fertility and moisture; otherwise, the height will be shorter. In low light intensities, the heights are generally taller. |
| 6) HEIGHT OF FIRST CAPSULE<br>The height of the first capsule from the ground to the bottom of the lowest capsule on the main stem | S32 = 58 cm<br>(Uvalde nursery, 2007)<br>Value based on an the average of a minimum of three plants (unit of measure: cm)<br>Distribution within Sesaco based on stable lines in the crossing program in 1999-2001 (Total number of samples tested = 2274) low = 20 cm; high 193 cm<br>1 = <54.6 cm; 52.7%<br>2 = <89.2 cm; 45.5%<br>3 = <123.8 cm; 1.5%<br>4 = <158.4 cm; 0.3%<br>5 = >158.3 cm; 0.1%<br>avg. = 54.2 cm, std = 14.3 | The measurement is made after the plants stop flowering. For plants that are not erect or have lodged, the plant should be picked up for the measurement. In most lines, the lowest capsule is on the main stem. True branches have capsules higher than on the main stem except when the flowers fall off the main stem. Occasionally, on weak branches, the lowest capsule is on the branches. There are lines that flower in the lower nodes late in the cycle, and, thus, the measure-ment should be taken after flowering ends. In many lines the first flower does not make a capsule, and, thus, this height may not be the same as the height of the first flower. The height is correlated to the length of time to flowering, the earlier the lower the height.<br>COMMENTS: see HEIGHT OF PLANT (Character No. 5) for effects of environmental factors |
| (7) CAPSULE ZONE LENGTH<br>The length of the capsule zone. The capsule zone extends from the bottom of the lowest capsule on the main stem to the top of the highest capsule on the main stem. | S32 = 89 cm<br>(Uvalde nursery, 2007)<br>Value based on an the average of a minimum of three plants (unit of measure: cm)<br>Distribution within Sesaco based on stable lines in the crossing program in 1999-2001 (Total number of samples tested = 2274) low = 18 cm; high = 188 cm<br>1 = <52 cm; 4.7%<br>2 = <86 cm; 53.5%<br>3 = <120 cm; 41.3%<br>4 = <154 cm; 0.5%<br>5 = >153.9 cm; 0.1%<br>avg. = 80.6 cm, std = 17.2 | The measurement is derived by subtracting the HEIGHT OF FIRST CAPSULE (Character No. 6) from the HEIGHT OF PLANT (Character No. 5).<br>COMMENTS: see HEIGHT OF PLANT (Character No. 5) for effects of environmental factors |
| (8) NUMBER OF CAPSULE NODES<br>The number of capsule nodes from the lowest capsule node to the highest node with capsules with viable seed on the main stem of the plant | S32 = 25<br>(Uvalde nursery, 2007)<br>Value based on an the average of a minimum of three plants (unit of measure: number)<br>Distribution within Sesaco based on stable lines in the crossing program in 1999-2001 (Total number of samples tested = 2154) low = 10; high = 54<br>1 = <18.8; 17.9%<br>2 = <27.6; 48.3%<br>3 = <36.4; 29.5%<br>4 = <45.2; 3.6%<br>5 = >45.1; 0.7%<br>avg. = 25.3, std = 6.4 | The count is made after the plants stop flowering. On opposite and alternate arranged leaves, each pair of leaves is counted as one node. In some lines, there are three leaves per node for at least part of the plant. In some plants, flowers may not have produced capsules on one or more of the leaf axils in a node. These nodes should still be counted. Nodes on the branches are not counted.<br>In years when the amount of moisture available to the plant is irregular, nodes can become very irregular, particularly on triple capsule lines. In the upper portions of the plant, it may become easier to count the capsule clusters and divide by 2. While it is possible to count nodes after leaves have fallen, it is much easier to count while the leaves are still on the plant.<br>COMMENTS: the number of nodes is dependent on the amount of moisture and |

TABLE II-continued

Characters Distinguishing the S32 Line

| Character | Rating | Methodology |
|---|---|---|
| | | fertility. Higher moisture and fertility increases the number of nodes. |
| (9) AVERAGE INTERNODE LENGTH WITHIN CAPSULE ZONE<br>The average internode length within the capsule zone | S32 = 3.6 cm (Uvalde nursery, 2007) Value based on an the average of a minimum of three plants (unit of measure: cm) Distribution within Sesaco based on stable lines in the crossing program in 1999-2001 (Total number of samples tested = 2145) low = 1.09 cm; high = 8.09 cm<br>1 = <2.49 cm; 6.2%<br>2 = <3.89 cm; 74.6%<br>3 = <5.29 cm; 18.6%<br>4 = <6.69 cm; 0.4%<br>5 = >6.68 cm; 0.1%<br>avg. = 3.35 cm, std = 0.66 | Divide the CAPSULE ZONE LENGTH (Character No. 7) by the NUMBER OF CAPSULE NODES (Character No. 8). COMMENTS: this length is dependent on the amount of moisture, fertility, and population. Increased values generally increase the length. In a high population, the length will only increase if there is adequate fertility and moisture; otherwise the length will be shorter. In low light intensities, the lengths are generally longer.<br>Past methodologies have measured the internode length at the middle of the capsule zone. Some have measured it at the median node and others at the median CAPSULE ZONE LENGTH. |
| (10) YIELD AT DRYDOWN<br>An extrapolation of the yield of a field by taking sample yields | S32 = 1,315 kg/ha (Uvalde nursery, 2007)<br>S32 = 1,059 kg/ha (Lorenzo nursery, 2007)[b]<br>Values based on the average of a minimum of three replications (unit of measure: kg/ha) Distribution within Sesaco based on stable lines in the crossing program in 1999-2001 (Total number of samples tested = 1828) low = 67 kg/ha high = 2421 kg/ha<br>1 = <537.8 kg/ha; 5.6%<br>2 = <1008.6 kg/ha; 15.6%<br>3 = <1479.4 kg/ha; 51.5%<br>4 = <1950.2 kg/ha; 25.8%<br>5 = >1950.1 kg/ha; 1.4%<br>avg. = 1114.6 kg/ha, std = 331.2 | On 3 replicated plots, when the plants are dry enough for direct harvest, cut a minimum of 1/5000 of a hectare (Sesaco uses 1/2620) in the plot and place the plants in a cloth bag. Thresh the sample in a plot thresher and weigh the seed. Multiply the weight by the appropriate multiplier based on area taken to provide the extrapolated yield in kg/ha.<br>In the Almaco thresher there is about 3% trash left in the seed. Since yields are comparative, there is no cleaning of the seed done before the computation. If other threshers have more trash, the seed should be cleaned before weighing. COMMENTS: yields increase with moisture and fertility. However, too high a moisture can lead to killing of plants. Too high fertility can lead to extra vegetative growth that may not lead to higher yields. The optimum population depends on the PLANT PHENOTYPE, Character No. 4 (BRANCHING STYLE, Character No. 1; NUMBER OF CAPSULES PER LEAF AXIL, Character No. 2; and MATURITY CLASS, Character No. 3) and row width. |
| (11) RESISTANCE TO DROUGHT<br>The relative amount of resistance to drought | S32: No data collected Average of a minimum of three plots of a subjective rating based on the following values:<br>0 to 8 scale<br>7 = Little effect from drought<br>4 = Medium effect from drought<br>1 = Considerable effect from drought<br>Intermediate values are used.<br>Distribution within Sesaco based on stable lines in the crossing program in 2000 (Total number of samples tested = 632) low = 0; high = 8<br>1 = <1.6; 0.8%<br>2 = <3.2; 28.0%<br>3 = <4.8; 36.1%<br>4 = <6.4; 34.5%<br>5 = >6.3; 0.6%<br>avg. = 4.1, std = 1.2 | In a year when there is a drought, this rating can be used to differentiate the effects of the different lines. This is a highly subjective rating requiring a rater that is familiar with the performance of the line under normal conditions. The rating is based on how the drought changes the line from normal. Thus, a short line that does not change significantly in a drought may have a higher rating than a tall line which is affected by the drought even though the taller line is taller in the drought than the short line. |

TABLE II-continued

Characters Distinguishing the S32 Line

| Character | Rating | Methodology |
|---|---|---|
| (12) LEAF LENGTH The length of the leaf blade from the base of the petiole to the apex of the leaf from the 5$^{th}$, 10$^{th}$, and 15$^{th}$ node pairs | S32: No data collected Value based on an the average of a minimum of three plants (unit of measure: cm) Distribution within Sesaco for 5$^{th}$ leaf based on stable lines in the crossing program in 2002 (Total number of lines tested = 196 with 711 samples) low = 13.8 cm; high = 42.5 cm 1 = <19.5 cm; 34.7% 2 = <25.3 cm; 48.0% 3 = <31.0 cm; 14.3% 4 = <36.8 cm; 1.5% 5 = >36.7 cm; 1.5% avg. = 21.5 cm, std = 4.4 Distribution within Sesaco for 10$^{th}$ leaf based on stable lines in the crossing program in 2002 (Total number of lines tested = 196 with 711 samples) low = 9.3 cm; high = 32.9 cm 1 = <14.0 cm; 22.4% 2 = <18.7 cm; 41.8% 3 = <23.5 cm; 20.9% 4 = <28.2 cm; 10.2% 5 = >28.1 cm; 4.6% avg. = 17.9 cm, std = 4.8 Distribution within Sesaco for 15$^{th}$ leaf based on stable lines in the crossing program in 2002 (Total number of lines tested = 196 with 711 samples) low = 4.4 cm; high = 26.2 cm 1 = <8.8 cm; 5.1% 2 = <13.1 cm; 42.9% 3 = <17.5 cm; 29.8% 4 = <21.8 cm; 15.8% 5 = >21.7 cm; 6.6% avg. = 14.3 cm, std = 4.2 | Select one leaf per node to measure from the 5$^{th}$, 10$^{th}$, and 15$^{th}$ node pairs from the base of the plant. All the leaves for one line should be collected at the same time. Some lines retain the cotyledons, and the cotyledon node does not count as a node pair. In some lines the lowest leaves abscise leaving a scar on the stem. Abscised nodes should be counted. In lines with alternate leaves, one node is counted for each pair of leaves. In some lines in parts of the plant there are three leaves per node which should be counted as one node. The leaves continue growing in the first few days after they have separated from the growing tip. The choosing of leaves should be done a minimum of 5 days after the 15$^{th}$ node has appeared. Timing is important, because the plants will begin to shed their lower leaves towards the end of their cycle. There are lines that have less than 15 nodes. In this case, the highest node should be taken and the node number annotated to the measurements. There can be as much as 6 mm difference between a green leaf and a dry leaf. The measurements can be done on a green or dry leaf as long as any comparison data with other lines is based on the same method. Generally, the lowest leaves increase in size until the 4$^{th}$ to 6$^{th}$ node and then they decrease in size. This applies to LEAF LENGTH (Character No. 12), LEAF BLADE WIDTH (Character No. 14), and PETIOLE LENGTH (Character No. 15). In few cases, LEAF BLADE LENGTH Character No. 13) can increase up the 10$^{th}$ node, but will decrease by the 15$^{th}$ node. Generally, the width will decrease at a greater rate than the length. COMMENTS: the length is dependent on the amount of moisture and fertility. Higher moisture and fertility increase the length. Leaf size also appears to be affected by light intensity. In Korea, the Korean lines have much larger leaves than in Oklahoma. In Korea, there is more cloud cover and a general haze than in Oklahoma. |
| (13) LEAF BLADE LENGTH The length of the leaf blade from the base of the leaf blade to the apex of the leaf from the 5$^{th}$, 10$^{th}$, and 15$^{th}$ node pairs | S32: No data collected Value based on an the average of a minimum of three plants (unit of measure: cm) Distribution within Sesaco for 5$^{th}$ leaf based on stable lines in the crossing program in 2002 (Total number of lines tested = 196 with 711 samples) low = 9.0 cm; high = 25.5 cm 1 = <12.3 cm; 14.3% 2 = <15.6 cm; 60.2% 3 = <18.9 cm; 20.9% 4 = <22.2 cm; 3.1% 5 = >22.1 cm; 1.5% avg. = 14.4 cm, std = 2.4 Distribution within Sesaco for 10$^{th}$ leaf based on stable lines in the crossing | See LEAF LENGTH (Character No. 12) on how to collect leaves. The measurement does not include PETIOLE LENGTH (Character No. 15). In some leaves the blade on one side of the petiole starts before the other side. This measure should start from the lowest blade side. There are leaves that have enations where a blade starts and then stops. The enations are not considered part of the leaf blade because they are very irregular from plant to plant and within a plant. COMMENTS: see LEAF LENGTH (Character No. 12) for effects of environment |

TABLE II-continued

Characters Distinguishing the S32 Line

| Character | Rating | Methodology |
|---|---|---|
| | program in 2002 (Total number of lines tested = 196 with 711 samples) low = 8.3 cm; high = 23.4 cm 1 = <11.3 cm; 18.9% 2 = <14.3 cm; 42.9% 3 = <17.4 cm; 25.0% 4 = <20.4 cm; 9.2% 5 = >20.3 cm; 4.1% avg. = 13.9 cm, std = 3.0 Distribution within Sesaco for 15$^{th}$ leaf based on stable lines in the crossing program in 2002 (Total number of lines tested = 196 with 711 samples) low = 4.2 cm; high = 20.7 cm 1 = <7.5 cm; 2.0% 2 = <10.8 cm; 36.7% 3 = <14.1 cm; 37.8% 4 = <17.4 cm; 16.3% 5 = >17.3 cm; 7.1% avg. = 12.0 cm, std = 3.0 | |
| (14) LEAF BLADE WIDTH The width of the leaf blade measured across the leaf blade at the widest point at the 5$^{th}$, 10$^{th}$, and 15$^{th}$ node pairs | S32: No data collected Value based on an the average of a minimum of three plants (unit of measure: cm) Distribution within Sesaco for 5$^{th}$ leaf based on stable lines in the crossing program in 2002 (Total number of lines tested = 196 with 711 samples) low = 3.4 cm; high = 31.0 cm 1 = <8.9 cm; 53.1% 2 = <14.4 cm; 33.7% 3 = <20.0 cm; 9.7% 4 = <25.5 cm; 2.6% 5 = >25.4 cm; 1.0% avg. = 9.6 cm, std = 4.3 Distribution within Sesaco for 10$^{th}$ leaf based on stable lines in the crossing program in 2002 (Total number of lines tested = 196 with 711 samples) low = 1.3 cm; high = 17.6 cm 1 = <4.6 cm; 69.4% 2 = <7.8 cm; 25.0% 3 = <11.1 cm; 4.6% 4 = <14.3 cm; 0% 5 = >14.2 cm; 1.0% avg. = 4.3 cm, std = 2.2 Distribution within Sesaco for 15$^{th}$ leaf based on stable lines in the crossing program in 2002 (Total number of lines tested = 196 with 711 samples) low = 0.7 cm; high = 6.0 cm 1 = <1.8 cm; 29.1% 2 = <2.8 cm; 48.0% 3 = <3.9 cm; 15.3% 4 = <4.9 cm; 4.6% 5 = >4.8 cm; 3.1% avg. = 2.3 cm, std 0.9 | See LEAF LENGTH (Character No. 12) on how to collect leaves. There are many leaves that are not symmetrical with lobbing on one side and not the other. The width should still be measured across the widest point on a line perpendicular to the main vein of the leaf. On some lines the width exceeds the length, particularly on lobed leaves. COMMENTS: see LEAF LENGTH (Character No. 12) for effects of environment The widest leaves are lobed. Normally, the leaves have turned from lobed to lanceolate by the 10$^{th}$ leaf with the exception of the tropical lines. |
| (15) PETIOLE LENGTH The length of the petiole from the base of the petiole to the start of the leaf blade at the | S32: No data collected Value based on an the average of a minimum of three plants (unit of measure: cm) | See LEAF BLADE LENGTH (Character No. 13) on how to collect leaves. In some leaves, the blade on one side of the petiole starts before the other side. This measure should end where the earliest blade starts. |

TABLE II-continued

Characters Distinguishing the S32 Line

| Character | Rating | Methodology |
|---|---|---|
| $5^{th}$, $10^{th}$, and $15^{th}$ node pairs | Distribution within Sesaco for $5^{th}$ leaf based on stable lines in the crossing program in 2002 (Total number of lines tested = 196 with 711 samples) low = 3.0 cm; high = 17.0 cm 1 = <5.8 cm; 35.2% 2 = <8.6 cm; 39.8% 3 = <11.4 cm; 19.4% 4 = <14.2 cm; 4.1% 5 = >14.1 cm; 1.5% avg. = 7.0 cm, std = 2.5 Distribution within Sesaco for $10^{th}$ leaf based on stable lines in the crossing program in 2002 (Total number of lines tested = 196 with 711 samples) low = 1.0 cm; high = 14.2 cm 1 = <3.6 cm; 53.6% 2 = <6.3 cm; 31.6% 3 = <8.9 cm; 11.7% 4 = <11.6 cm; 2.0% 5 = >11.5 cm; 1.0% avg. = 4.0 cm, std = 2.1 Distribution within Sesaco for $15^{th}$ leaf based on stable lines in the crossing program in 2002 (Total number of lines tested = 196 with 711 samples) low = 0.2 cm; high = 7.4 cm 1 = <1.6 cm; 38.8% 2 = <3.1 cm; 41.8% 3 = <4.5 cm; 13.3% 4 = <6.0 cm; 3.1% 5 = >5.9 cm; 3.1% avg. = 2.3 cm, std = 1.3 | There are leaves that have enations where a blade starts and then stops. The enations are not considered part of the leaf blade because they are very irregular from plant to plant and within a plant and should be measured as part of the petiole. COMMENTS: see LEAF LENGTH (Character No. 12) for effects of environment |
| (16) NUMBER OF CARPELS PER CAPSULE The predominant number of carpels per capsule in the middle half of the capsule zone | S32 = 2 (All crops, all nurseries) Subjective rating based on the following values: 2 = bicarpellate 3 = tricarpellate 4 = quadricarpellate (unit of measure: actual number Distribution within Sesaco based on the introductions received in 1982-2001 (Total number of samples tested = 2702) 2 = 97.6% 3 = 0.0004% 4 = 2.3% Sesaco has not developed lines with more than 2 carpels. | The rating can be taken from about 60 days after planting to all the way to the end of the crop. There are many plants with mixed number of carpels as follows: 1. Some bicarpellate plants will have one or more nodes near the center of the capsule zone that have tri- and/or quadricarpellate capsules and vice versa. 2. Most tri- and quadri-carpellate plants will begin and end with bicarpellate nodes. 3. Some plants have only one carpel that develops. These capsules are generally bent, but on examination the $2^{nd}$ carpel can be seen. 4. On all types, flowers may coalesce and double or triple the number of carpels. 5. On the seamless gene plants (gs/gs) the false membranes do not form locules. These are still considered bicarpellate. |
| (17) CAPSULE LENGTH FROM 10cap TEST The length of the capsule from the bottom of the seed chamber to the top of the seed chamber from the outside of the capsule. The tip of the capsule is not included in the measurement. | S32 = 2.14 cm (All experimental nurseries, 1997-2006) Value based on the average of a minimum of three samples of the length taken on the median capsule in a 10 capsule sample (unit of measure: cm) Distribution within Sesaco based on 10cap test in all | After the plants are physiologically mature, take 2 capsules from five plants from the middle of the capsule zone. On three capsule per leaf axil lines, one central capsule and one axillary capsule should be taken from the same leaf axil. The measurement is taken on the median capsule of single capsule lines and on the median central capsule on three capsule lines. The measurement is taken on dry capsules because the length can shorten as much as one mm on drydown. |

TABLE II-continued

Characters Distinguishing the S32 Line

| Character | Rating | Methodology |
|---|---|---|
| | nurseries in 1997-2002 (Total number of lines tested = 1,613 with 8,285 samples) low = 1.3 cm; high = 4.5 cm 1 = <1.94 cm; 2.7% 2 = <2.58 cm; 67.9% 3 = <3.22 cm; 27.2% 4 = <3.86 cm; 1.9% 5 = >3.85 cm; 0.3% avg. = 2.44 cm, std = 0.33 | The 10 capsules can be sampled from physiological maturity through complete drydown without an effect on this character. Generally, the capsules in the middle of the capsule zone are the longest on the plant. COMMENTS: the length of the capsule is dependent on the amount of moisture, fertility, and population. Higher moisture and fertility increase the length. Higher population decreases the length even with adequate moisture/fertility. |
| (18) SEED WEIGHT PER CAPSULE FROM 10cap TEST The weight of the seed in a capsule from the center of the capsule zone | S32 = 0.227 g (All experimental nurseries, 1997-2006) Value based on the average of a minimum of three samples of the weight of 10 capsules (unit of weight: grams) Distribution within Sesaco based on 10cap test in all nurseries in 1997-2002 (Total number of lines tested = 1,613 with 8,285 samples) low = 0.053 g; high = 0.476 g 1 = <0.138 g; 1.3% 2 = <0.222 g; 47.6% 3 = <0.307 g; 50.6% 4 = <0.391 g; 1.1% 5 = >0.390 g; 0.1% avg. = 0.221 g, std = 0.039 | See CAPSULE LENGTH FROM 10CAP TEST (Character No. 17) for collection of capsules. The capsules should be dried, the seed threshed out, and the seed weighed. The 10 capsules can be sampled from physiological maturity through complete drydown without an effect on this character. After drydown, only capsules with all their seed are taken. Thus, this test cannot be done on shattering lines after drydown. Generally, the capsules in the middle of the capsule zone have the highest seed weight per capsule on the plant. COMMENTS: see CAPSULE LENGTH FROM 10CAP TEST (Character No. 17) for the effects of environmental factors. |
| (19) CAPSULE WEIGHT PER CAPSULE FROM 10cap TEST The weight of the capsule from the center of the capsule zone after the seed has been removed | S32 = 0.147 g (All experimental nurseries, 1997-2006) Value based on the average of a minimum of three samples of the weight of 10 capsules (unit of measure: grams) Distribution within Sesaco based on 10cap test in all nurseries in 1997-2002 (Total number of lines tested = 1,613 with 8,285 samples) low = 0.059 g; high = 0.395 g 1 = <0.126 g; 22.6% 2 = <0.193 g; 69.1% 3 = <0.261 g; 8.2% 4 = <0.328 g; 0.9% 5 = >0.327 g; 0.6% avg. = 0.152 g, std = 0.036 | See CAPSULE LENGTH FROM 10CAP TEST (Character No. 17) for collection of capsules. The capsules should be dried, the seed threshed out, and the capsules weighed. At times the peduncle can still be attached to the capsules. The peduncles should be removed and not weighed. The 10 capsules can be sampled from physiological maturity through complete drydown without an effect on this character. Generally, the capsules in the middle of the capsule zone have the highest capsule weight per capsule on the plant. COMMENTS: see CAPSULE LENGTH FROM 10CAP TEST (Character No. 17) for the effects of environmental factors. |
| (20) CAPSULE WEIGHT PER CM OF CAPSULE The weight of a capsule per cm of capsule from the center of the capsule zone | S32 = 0.069 g (All experimental nurseries, 1997-2006) Value based on the average of a minimum of three samples of the weight per cm of 10 capsules (unit of measure: grams) Distribution within Sesaco based on 10cap test in all nurseries in 1997-2002 (Total number of lines tested = 1,613 with 8,285 samples) low = 0.027 g; high = 0.123 g 1 = <0.046 g; 8.2% 2 = <0.065 g; 55.5% 3 = <0.085 g; 36.5% 4 = <0.104 g; 4.4% | The weight is derived by dividing the CAPSULE WEIGHT PER CAPSULE FROM 10CAP TEST (Character No. 19) by the CAPSULE LENGTH FROM 10CAP TEST (Character No. 17). The 10 capsules can be sampled from physiological maturity through complete drydown without an effect on this character. COMMENTS: this character is used instead of capsule width. Capsule width is difficult to measure because there are so many variables in a capsule. In a bicarpellate capsule, the width differs when measuring across one carpel or both carpels. Capsules can also vary through the length of the capsule by being substantially narrower at the bottom, middle or top of the capsule. In 1997, four widths were measured on each capsule |

TABLE II-continued

Characters Distinguishing the S32 Line

| Character | Rating | Methodology |
|---|---|---|
| | 5 = >0.103 g; 0.5% avg. = 0.063 g, std = 0.012 | and then averaged. This average had a very high correlation to the capsule weight per cm of capsule. See CAPSULE LENGTH FROM 10CAP TEST (Character No. 17) for effects of environmental factors |
| (21) VISUAL SEED RETENTION Amount of seed in most of the capsules in the middle half of the capsule zone when the plant(s) are dry enough for direct harvest with a combine | S32 = I (All crops, all nurseries) Subjective rating based on the following values: X = <50% seed retention (unsuitable for direct harvest) C = 50-74% seed retention (unsuitable for direct harvest, but may segregate V or above in future generations) V = >74% seed retention (sufficient seed retention for 10cap testing) W = >74% seed retention on weathering in field after rains and/or winds I = in using the "drum test" the seed in the capsules do not rattle and >85% of the capsules on the plant(s) harvested have visible seed in the tips of the capsules four or more weeks after the ideal harvest time. The "I" rating is used for all of the capsules on the plant. '+' and '−' modifiers can be used. | This rating is used for plants that are being selected for advanced testing whether individually or in a bulk with all the plants having the same level of seed retention. Most "X" plants can be identified from the first capsule that dries since the seed will begin falling out immediately. A "C" (close to V) plant will have some capsules with seed and some without. A "V" (visual shatter resistance) plant can be identified when the first 50% of the capsules have dried, but a "V+" rating should not be used until the complete plant is dry and most of the capsules are showing seed retention. Some "V" plants can be upgraded to "W" after the dry capsules have been subjected to weather (rain and/or wind) "V" and "W" become non-dehiscent only after 10cap testing with about an 80% passing rate. 10cap testing is done on "I" selections have had about a 99% passing rate. The "drum test" consists of placing the fingers from one hand about ½ inch from the center of the main stem and then striking the stem alternately with one finger and then the other finger in rapid succession. The human ear can perceive degree of rattling over a range. IND is defined as having no rattle. Degree of rattle in this test correlates with loss of increasing amounts of seed as capsules are exposed to weather conditions. COMMENTS: the ratings above should be made under normal conditions (600 mm of annual rainfall and 30 kg/ha of nitrogen) through high moisture/fertility conditions. In drought or very low fertility conditions, it has been observed that there is less seed retention. In addition, high populations may lead to low moisture or fertility causing less seed retention. If unusual environmental conditions are present, the effects should be taken into consideration prior to rating. |
| (22) SHAKER SHATTER RESISTANCE FROM 10cap TEST The amount of seed retention after the capsules are dry, inverted, and put through a shaker (10 capsule sample) | S32 = 77.2% (All experimental nurseries, 1997-2006) Value based on the average of a minimum of three samples of the percentage of seed retained in 10 capsules (unit of measure: Actual Number expressed as percentage) Distribution within Sesaco based on 10cap test in all nurseries in 1997-2002 (Total number of lines tested = 1,613 with 8,285 samples) low = 0; high = 100 1 = <20; 12.9% 2 = <40; 6.9% 3 = <60; 23.4% | See CAPSULE LENGTH FROM 10CAP TEST (Character No. 17) for collection of capsules. The capsules should be dried and inverted. The capsules and any seed that has fallen out should then be placed in flasks on a reciprocal shaker with a 3.8 cm stroke with 250 strokes/min for 10 minutes (see U.S. Pat. No. 6,100,452). The seed that comes out of the capsules should be weighed as 'out seed.' The retained seed should be threshed out of the capsules and weighed to compute the 'total seed'. The shaker shatter resistance is computed as a percentage as follows: (total seed − out seed)/total seed. The 10 capsules can be sampled from physiological maturity through complete drydown without an effect on this character for shatter resistant types. When taking capsules after drydown, only capsules with all their seed are taken. Thus, this test |

TABLE II-continued

Characters Distinguishing the S32 Line

| Character | Rating | Methodology |
| --- | --- | --- |
| | 4 = <80; 47.7%<br>5 = >79.9; 9.2%<br>avg. = 55.9%, std = 23.9 | cannot be done on shattering lines after drydown.<br>COMMENTS: The ratings above should be made under normal conditions through high moisture/fertility conditions. In drought or very low fertility conditions, it has been observed that there is less seed retention. In additions, high populations may lead to low moisture or fertility causing there is less seed retention. If unusual environmental conditions are present, the effects should be taken into consideration prior to rating. Lines with shaker shatter resistance >64.9% are known as non-dehiscent lines (see U.S. Pat. No. 6,100,452). |
| (23) CAPSULE SHATTERING TYPE<br>Amount of seed retention in a line or plant | S32 = SR<br>(All crops, all nurseries)<br>Subjective rating based on the following values:<br>SUS = Super-shattering (<2 visual seed retention - equates to <25%)<br>SHA = Shattering (<4 visual seed retention - equates to <50%)<br>SSH = Semi-shattering (4-6 visual seed retention - equates to 50 to 75%)<br>SR = Shatter resistant (a numeric rating>6 visual seed retention without id or gs alleles - equates to >75%; an alphabetical rating of V, W, or I)<br>ID = Indehiscent (presence of id/id with capsule closed)<br>IDO = Indehiscent (presence of id/id with capsule open at tip)<br>GS = Seamless (presence of gs/gs with capsule closed)<br>GSO = Seamless (presence of gs/gs with capsule open at tip) | The rating is based on visual observations as to seed retention as the plants remain standing in the field without shocking.<br>GS plants can be identified while the plant is putting on capsules or at drydown because the carpels in the capsules do not form false membranes. There are plants that will have capsules with false membranes on the lower and upper nodes but most of the capsules show no false membranes.<br>ID plants can be identified during the growing season in that they have enations on the bottoms of the leaves. At dry down they are more difficult to distinguish from other lines that have closed capsules (other than GS). There is less of a suture than other capsule types.<br>SUS, SHA, SSH, and SR are defined by VISUAL SEED RETENTION (Character No. 21).<br>COMMENTS: Most environmental factors do not have much of an effect on capsule shattering type other than to make it more difficult to distinguish in the overlap zone. Generally, higher moisture, higher fertility, and lower populations will decrease the shattering a small amount - less than 10%.<br>The wind can have a large effect in decreasing the amount of seed retention. Rain, dew and fog can also reduce seed retention. |
| (24) NON-DEHISCENT TEST<br>A line that has passed the non-dehiscent test of having shaker shatter resistance >64.9% is considered an ND line in accordance with U.S. Pat. No. 6,100,452. | S32 = ND<br>(All crops, all nurseries)<br>Subjective rating based on the following values:<br>ND = Non-dehiscent line<br>XX = Line that does not pass the non-dehiscent test<br>ND distribution within Sesaco based on 10cap test in all nurseries in 1997-2006<br>(Total number of samples tested = 10,905)<br>ND = 53.6%<br>XX = 46.4% | Lines are designated as ND only after they have undergone a minimum of 3 shaker shatter resistance tests. In order to be considered an ND variety, the line must pass the ND threshold in multiple nurseries for multiple years. |
| (25) IMPROVED NON-DEHISCENT VISUAL RATING<br>Amount of seed in most of the capsules in the plants in a plot four or more weeks after the ideal harvest time. | S32 = 7.33<br>(Uvalde nursery, 2006)<br>S32 = 7.08<br>(Lorenzo nursery, 2006)<br>S32 = 7.35<br>(Lorenzo nursery, 2007)<br>Value based on the average on a minimum of three plots of a subjective | This rating is used for a plot or field that is being evaluated.<br>The data is taken four or more weeks after the ideal harvest time. See DAYS TO DIRECT HARVEST (Character No. 30). Estimate the percentage of capsules that have visible seed at the top. In the beginning in order to develop an eye for the rating, the evaluator should observe all |

TABLE II-continued

Characters Distinguishing the S32 Line

| Character | Rating | Methodology |
|---|---|---|
| | rating based on the percentage of capsules with visible seed retention<br>8 < 100%<br>7 < 85%<br>6 < 70%<br>5 > 55%<br>Z < 55%<br>'+' and '−' modifiers can be used. For averages, 0.33 is added for a '+' and 0.33 is subtracted for a '−' eg., "7+" = 7.33.<br>(Total number of lines tested = 288 with 801 samples in 2006)<br>low = 2.97; high = 7.33<br>1 = <6.0; 2.1%<br>2 = <6.5; 20.8%<br>3 = <7.0; 13.2%<br>4 = <7.5; 63.9%<br>5 = >7.5; 0%<br>avg. = 6.77, std = 0.54<br>Note: The percentage of lines between 7.0 and 7.6 is very high because Sesaco has established a new threshold for a new variety of IND > 6.9 and only lines that are IND or segregating IND are rated. | of the capsules and rate each of them; get a counts of those with visible seeds and a count of total capsules; and compute a percentage. Once the evaluator is skilled, there is no need to count the capsules. There is a very high correlation between this rating upon visual evaluation and the amount of rattling generated by the "drum test" defined above.<br>Although retention can vary from plant to plant and even within a plant, the overall rating is correlatable with IND.<br>In crossing between lines, in early generations there is a segregation of IND plants and non-IND plants. In this case the plot is given a rating of the majority of plants while the plants selected can have a higher rating which is reflected in VISUAL SEED RETENTION. The ratings that are cited in this character are for plots, but a ratings of 7 or 8 are only given if over 90% of the plants have the higher rating. |
| (26) IMPROVED NON-DEHISCENCE TEST<br>An ND line that passes the rattle test and has a visual IND rating >6.99 is considered IND. A method for traditional breeding of an IND line is described in concurrently filed U.S. Patent Application Ser. No. _____ (Attorney Docket Number SESA 3200 PTUS). ND and IND lines should not have id or gs alleles. | S32 = IND<br>(All crops, all nurseries<br>Subjective rating based on the following values:<br>IND = Improved Non-dehiscent line<br>ZZ = Line that does not pass the non-dehiscent test<br>Distribution within Sesaco based on visual IND (Total number of lines tested = 1,934 in all nurseries from 2005 to 2007)<br>IND = 9.5%<br>ZZ = 90.5% | Varieties were designated as IND after they demonstrated the defined characteristics with statistically significant data. |
| (27) DAYS TO FLOWERING<br>Number of days from planting until 50% of the plants are flowering | S32 = 42 days<br>(Uvalde nursery, 2007)<br>Value based on the average of a minimum of three plots of the number of days (unit of measure: days)<br>Distribution within Sesaco based on lines in Uvalde nursery in 2000-2001<br>(Total number of samples tested = 1831)<br>low = 33 days; high = 89 days<br>1 = <44.2 days; 87.9%<br>2 = <55.4 days; 7.8%<br>3 = <66.6 days; 2.4%<br>4 = <77.8 days; 1.7%<br>5 = >77.7 days; 0.2%<br>avg. = 40.9 days, std = 6.3 | The vegetative phase in sesame is from the time of planting to the start of flowering.<br>This data is taken as a date and later converted to number of days. Flowering is defined as flowers that are open - not buds.<br>COMMENTS: flowering can be accelerated by drought and it can be delayed by higher moisture and/or fertility. Higher heat units will decrease the days to flowering.<br>Some lines are photosensitive and will only begin flowering at a certain number of hours of daylight.<br>Start of flowering does not always equate to start of capsule formation. Many lines will flower and not set capsules from the first flowers. |
| (28) DAYS TO FLOWER TERMINATION<br>Number of days from planting until 90% of the plants have stopped flowering | S32 = 88 days<br>(Uvalde nursery, 2007)<br>Value based on the average of a minimum of three plots of the number of days (unit of measure: days)<br>Distribution within Sesaco | The reproductive phase of sesame is from the start to the end of flowering.<br>This data is taken as a date and later converted to number of days. Flowering is defined as flowers that are open - not buds. At the end of the flowering period, the rate that a plant puts on open flowers is reduced. Thus, there can be more than |

TABLE II-continued

Characters Distinguishing the S32 Line

| Character | Rating | Methodology |
|---|---|---|
| | based on lines in Uvalde nursery in 2000-2001 (Total number of samples tested = 2668) low = 61 days; high = 114 days 1 = <71.6 days; 21.1% 2 = <82.2 days; 61.5% 3 = <92.8 days; 15.9% 4 = <103.4 days; 0.8% 5 = >103.3 days; 0.8% avg. = 77.1 days, std = 6.9 | 10% of plants with buds and still have reached this measure since there will not be more than 10% with open flowers on any one day. The measure is based on the number of plants and not the number of flowering heads. The branches will stop flowering before the main stem, and thus the plot will appear like there are more plants not flowering. COMMENTS: flower termination can be accelerated by lower moisture and/or fertility, and it can be delayed by higher moisture and/or fertility. Higher heat units will decrease the DAYS TO FLOWER TERMINATION. It is known that there are lines that stop flowering sooner than expected in northern latitudes, but it is not known if this is due to shorter photoperiod or cool temperatures. |
| (29) DAYS TO PHYSIOLOGICAL MATURITY Number of days from planting until 50% of the plants reach physiological maturity | S32 = 108 (Uvalde nursery, 2007) Value based on the average of a minimum of three plots of the number of days (unit of measure: days) Distribution within Sesaco based on lines in Uvalde nursery in 2000-2001 (Total number of samples tested = 2374) low = 77 days; high = 140 days 1 = <89.6 days; 16.8% 2 = 102.2 days; 58.0% 3 = <114.8 days; 23.6% 4 = <127.4 days; 1.4% 5 = >127.3 days; 0.2% avg. = 97.1 days, std = 7.1 | The ripening phase of sesame is from the end of flowering until physiological maturity. This data is taken as a date and later converted to number of days. Physiological maturity (PM) is defined as the point at which ¾ of the capsules have seed with final color. In most lines, the seed will also have a seed line and tip that are dark. COMMENTS: The concept of physiological maturity in sesame was developed by M. L. Kinman (personal communication) based on the concept of determining the optimum time to cut a plant and still harvest 95-99% of the potential yield. When the seed has final color, the seed can germinate under the proper conditions. If the plant is cut at physiological maturity, most of the seed above the ¾ mark will go to final color and are mature enough to germinate, but will not have as much seed weight. Since in even a fully mature plant, there is less seed weight made at the top of the plant, this loss of seed weight does not seriously affect the potential seed weight of the plant. Although present harvest methods let the plants mature and go to complete drydown, PM is important because after that point, the crop is less susceptible to yield loss due to frost or disease. The PM is also important if the crop is to be swathed or harvest aids are to be applied. Physiological maturity can be accelerated by lower moisture and/or fertility, and it can be delayed by higher moisture and/or fertility. Higher heat units will decrease the days to physiological maturity. Cool weather can delay physiological maturity. |
| (30) DAYS TO DIRECT HARVEST Number of days from planting until there is enough drydown for direct harvest | S32 = 129 (Uvalde nursery, 2007) Value based on the average of a minimum of three plots of the number of days (unit of measure: days) Distribution within Sesaco based on lines in all nurseries from 2004 tthrough 2006 (Total number of samples tested = 1,998) | The drying phase of sesame is from physiological maturity until direct harvest. This data is taken as a date and later converted to number of days. Direct harvest is defined as the date at which the plants are dry enough for combining seed at 6% or less moisture. Over 99% of the sesame in the world is harvested by hand before the plant completely dries down. The plants should be dry below where the cutter bar of the combine will hit the plants. In many lines, 15-20 cm from the ground can be green without an effect on |

TABLE II-continued

Characters Distinguishing the S32 Line

| Character | Rating | Methodology |
|---|---|---|
| | low = 103 days; high = 161 days<br>1 = <114.6 days; 3.3%<br>2 = <126.2 days; 13.3%<br>3 = <137.8 days; 32.1%<br>4 = <149.4 days; 44.2%<br>5 = >149.3 days; 7.2%<br>avg. = 136.7 days, std = 10.3 | the moisture of the seed. In taking the data on a plot, the plants at the aisle have more moisture and fertility available and will drydown later. The same is true for plants within the plot that have a gap of half a meter between plants. These plants should be disregarded in taking the data. In addition, there are few farmer fields that dry down uniformly because of varying soils and moisture. There is a certain amount of green that can be combined and still attain the proper moisture. The amount of green allowable is also dependent on the humidity at the day of combining-the lower the humidity the higher the amount of allowable green.<br>COMMENTS: This date is the most variable number of days that define the phenology of sesame because weather is so important. In dry years with little rainfall, the plants will run out of moisture sooner and will dry down faster than in years with more rainfall. Fields that are irrigated by pivots will generally dry down faster than fields with flood or furrow irrigation because pivots do not provide deep moisture. Fields with less fertility will drydown faster than fields with high fertility. Fields with high populations will dry down faster than fields with low populations. In low moisture situations lines with a strong taproot will dry down later than lines with mostly shallow fibrous roots. |
| (31) LODGING RESISTANCE<br>The amount of lodging | S32 = 6.28<br>(Uvalde nursery 2007);<br>S32 = 7.08<br>(Lorenzo nursery, 2007)<br>Average of a minimum of three plots of a subjective rating based on the following values:<br>0 to 8 rating<br>8 = no lodging<br>7 = Less than 5% of plants lodged<br>4 = 50% of plants lodged<br>1 = All plants lodged<br>Intermediate values are used.<br>Distribution within Sesaco based on lines in Uvalde and Lorenzo nurseries in 2007<br>(Total number of samples tested = 1061)<br>low = 1.0; high = 8.0<br>1 = <2.4; 3.1%<br>2 = <3.8; 6.9%<br>3 = <5.2; 22.6%<br>4 = <6.6; 18.9%<br>5 = >8.0; 48.4%<br>avg. = 6.1, std = 1.7 | The data is taken after physiological maturity (see DAYS TO PHYSIOLOGICAL MATURITY - Character No. 29) and before direct harvest (see DAYS TO DIRECT HARVEST - Character No. 30). Lodging that occurs after direct harvest in nurseries would not be a factor in commercial sesame.<br>There are three types of lodging: where the plants break at the stem, where the plants bend over but do not break, and where the plants uproot and bend over. When a plant breaks over, it will rarely produce any new seed, and the existing seed may or may not mature. If there is a total break, there is no hope, but if there is still some active stem translocation through the break, there can be some yield recovery. The main causes for uprooting of plants are shallow root systems and fields that have just been irrigated, creating a soft layer of soil. When a plant bends over early in development, some lines adapt better than others in terms of having the main stems turn up and continue flowering. The tips of the branches are usually matted under the canopy and will rarely turn up, but new branches can develop. As the plants go to drydown and the weight of the moisture is lost, many of the bent plants will straighten up making the crop easier to combine.<br>COMMENTS: The major cause of lodging is the wind. In areas where there are constant winds such as in Oklahoma and northern Texas, the plants adjust by adding more lignins to the stems and it takes a stronger wind to cause lodging than in areas such as Uvalde where there normally only breezes unless there is a strong front or thunderstorm that passes through. In areas with more root rots, the |

TABLE II-continued

Characters Distinguishing the S32 Line

| Character | Rating | Methodology |
|---|---|---|
| | | stems are weak and it takes little wind to lodge the plants. |
| (32) SEED COLOR<br>The color of the seed coat | S32 = BF<br>(All crops, all nurseries)<br>Subjective rating based on the following values:<br>WH = White<br>BF = Buff<br>TN = Tan<br>LBR = Light brown<br>GO = Gold<br>LGR = Light gray<br>GR = Gray<br>BR = Brown<br>RBR = Reddish brown<br>BL = Black<br>Distribution within Sesaco based on seed harvested in all nurseries in 1982-2001<br>(Total number of samples tested = 161,809)<br>WH = 0.8%<br>BF = 74.8%<br>TN = 9.0%<br>LBR = 1.4%<br>GO = 1.5%<br>LGR = 0.6%<br>GR = 1.4%<br>BR = 6.5%<br>RBR = 0.6%<br>BL = 3.5% | This data is taken in the laboratory with the same lighting for all samples. The seed from the whole plant is used.<br>Seed coat color is taken on mature seeds. If there is any abnormal termination, the colors are not quite as even. The color of immature seed varies. Usually light seeded lines have tan to light brown immature seed; tan, light brown, gold, brown light gray, and gray lines have lighter immature seed; black lines can have tan, brown, or gray immature seed. Usually, moisture, fertility, population and light intensity do not have an effect on seed coat color. Light colored seeds in a drought may have a yellowish tinge. Seeds in some lines in the tan, light brown and gold range can change from year to year among themselves. |
| (33) SEED WEIGHT - 100 SEEDS FROM 10cap TEST<br>Weight of 100 seeds taken from the 10cap tests which are taken from the middle of the plant. | S32 = 0.312 g<br>(All experimental nurseries, 1997-2006)<br>Value based on the average of a minimum of three samples of the weight of 100 seeds from the 10 capsules (unit of weight: grams)<br>Distribution within Sesaco based on stable lines in all nurseries in 1997-2002<br>(Total number of lines tested = 820 with 2,899 samples)<br>low = 0.200 g; high = 0.455 g<br>1 = <0..251 g; 10.1%<br>2 = <0.302 g; 48.4%<br>3 = <0.353 g; 34.0%<br>4 = <0.404 g; 7.2%<br>5 = >0.403 g; 0.2%<br>avg. = 0.298 g, std = 0.04 | See CAPSULE LENGTH FROM 10CAP TEST (Character No. 17) for collection of capsules.<br>Count out 100 seeds and weigh. The seed must be dry.<br>COMMENTS: the weight increases with higher moisture/fertility. Generally, the weight of the seed from the whole plant is lighter than the seed weight taken from the 10cap test. |
| (34) COMPOSITE KILL RESISTANCE<br>The amount of plants killed by root rots in the Sesaco nurseries | S32 = 5.94<br>(Uvalde nursery, 2007);<br>S32 = 6.25<br>(Lorenzo nursery, 2007)<br>Average of a minimum of three plots of a subjective rating based on the following values: Ratings are based on the number of plants killed in a plot. Before physiological maturity (PM), the following ratings are used:<br>1 = >90% kill before DAYS TO FLOWERING TERMINATION (Character No. 28)<br>2 = >90% kill between DAYS TO FLOWERING TERMINATION (Character No. 28) and DAYS TO | On the week a plot reaches PM, a rating is assigned. The ratings are then taken for 2 additional weeks. The three ratings are averaged for a final kill rating. For example, if a plot has a final kill of 766, the average for the plot will be 6.33. When a value of 1 or 2 is assigned, there are no additional ratings and there is no averaging.<br>There are three root diseases that affect sesame in Texas: *Fusarium oxysporum*, *Macrophomina phaseoli*, and *Phytophtora parasitica*. Between 1988 and the present, spores of these three have been accumulated in one small area (1 square km) north of Uvalde, and thus it is an excellent screening area for the diseases. Although each root rot attacks sesame in a different way with different symptoms, no effort is made to differentiate which disease is the culprit in each plot. |

TABLE II-continued

Characters Distinguishing the S32 Line

| Character | Rating | Methodology |
|---|---|---|
| | PHYSIOLOGICAL MATURITY (Character No. 29) After PM, the following ratings are used: 3 = >90% kill 4 = 50 to 89% kill 5 = 25 to 49% kill 6 = 10 to 24% kill 7 = less than 10% kill 8 = no kill Distribution within Sesaco based on lines in Uvalde nursery in 2000-2001 (Total number of samples tested = 3045) low = 1.00; high = 8.00 1 = <1.6; 1.7% 2 = <3.2; 16.7% 3 = <4.8; 38.7% 4 = <6.4; 31.2% 5 = >6.3; 11.6% avg. = 4.52, std = 1.49 | Pathological screenings in the past have found all 3 pathogens present in dead plants. COMMENTS: normally, the ratings will decrease a maximum of one value per week. There is an overlap between any two ratings, but this is overcome to a certain extent by using three ratings over 2 weeks. The amount of kill is usually increased with any type of stress to the plants. Drought can increase the amount of *Macrophomina*; too much water can increase the amount of *Phytophtora*; high temperatures and humidity can increase the amount of *Fusarium* and *Phytophtora*. High population can increase all three diseases. The ratings for any one year can be used to compare lines grown in that year, but should not be used to compare lines grown in different years. The amount of disease in any one year is highly dependent on moisture, humidity, and temperatures. |
| (35) RESISTANCE TO *FUSARIUM* WILT (*F. oxysporum*) Amount of resistance to *Fusarium* wilt | S32 = NT Average of a minimum of three plots of a subjective rating based on the following values: 0 to 8 scale of the % of infected plants<br><br>8 = Zero disease 7 = <10% infected 4 = 50% infected 1 = >90% infected 0 = all infected Intermediate values are used. NT = not tested NEC = no economic damage - not enough disease to do ratings | Ratings can be done in several ways: 1. Take ratings after the disease is no longer increasing 2. Take ratings on consecutive weeks until disease is no longer increasing and average ratings. 3. Take periodic ratings and average ratings. COMMENTS: *Fusarium* has been a problem in South Texas, particularly on fields that have been planted with sesame before. Normally, only the COMPOSITE KILL RESISTANCE (Character No. 34) rating is taken. |
| (36) RESISTANCE TO *PHYTOPHTORA* STEM ROT (*P. parasitica*) Amount of resistance to *Phytophtora* stem rot | S32 = NT Subjective rating See Values for *Fusarium* | See Methodology for RESISTANCE TO *FUSARIUM* WILT (Character No. 35) COMMENTS: *Phytophtora* has been a problem in Arizona and Texas, particularly on fields that have been over-irrigated. Normally, only the COMPOSITE KILL RESISTANCE (Character No. 34) rating is taken. |
| (37) RESISTANCE TO CHARCOAL ROT (*Macrophomina phaseoli*) Amount of resistance to Charcoal rot | S32 = NT Subjective rating See Values for *Fusarium* | See Methodology for RESISTANCE TO *FUSARIUM* WILT (Character No. 35) COMMENTS: *Macrophomina* has been a problem in Arizona and Texas, particularly on fields that go into a drought. Normally, only the COMPOSITE KILL RESISTANCE (Character No. 34) rating is taken. |
| (38) RESISTANCE TO BACTERIAL BLACK ROT (*Pseudomonas sesami*) Amount of resistance to bacterial black rot | S32 = 8.00 (Uvalde nursery, 2004) Average of a minimum of three plots of a subjective rating based on the following values: 0 to 8 scale of the % of infected plants 8 = Zero disease 7 = <10% infected 4 = 50% infected 1 = >90% infected 0 = all infected Intermediate values are used. | See Methodology for RESISTANCE TO *FUSARIUM* WILT (Character No. 35) COMMENTS: this disease occurs occasionally when there is continual rainy weather with few clouds. In most years, the disease abates once the weather changes. No economic damage has been noticed. |

TABLE II-continued

Characters Distinguishing the S32 Line

| Character | Rating | Methodology |
|---|---|---|
| | NT = not tested<br>NEC = no economic<br>damage - not enough<br>disease to do ratings<br>Distribution within Sesaco<br>based on lines in Uvalde<br>nursery in 2004<br>(Total number of samples<br>tested = 593)<br>low = 4.00; high = 8.00<br>1 = <2.4; 0.0%<br>2 = <3.8; 0.0%<br>3 = <5.2; 8.6%<br>4 = <6.6; 16.0%<br>5 = >6.5; 75.4%<br>avg. = 7.13, std = 1.00 | |
| (39) RESISTANCE TO<br>SILVERLEAF WHITE<br>FLY (*Bemisia*<br>*argentifolii*)<br>Amount of resistance to<br>the silverleaf white fly | S32 = NEC<br>(Uvalde nursery, 2006)<br>Average of a minimum of<br>three plots of a subjective<br>rating based on the<br>following values:<br>0 to 8 scale of the<br>% of infected plants<br>0 to 8 scale<br>8 = Zero insects<br>7 = Few insects<br>4 = Many insects<br>1 = Insects killing the<br>plants<br>Intermediate values are<br>used.<br>NT = not tested<br>NEC = no economic<br>damage - not enough<br>insects to do ratings | Ratings can be done in several ways:<br>1. Take ratings after the insects are no<br>longer increasing.<br>2. Take ratings on consecutive weeks<br>until insects are no longer increasing and<br>average ratings.<br>3. Take periodic ratings and average<br>ratings.<br>COMMENTS: there have been very<br>few years (1991-1995) where the<br>incidence of silverleaf white fly has<br>affected nurseries or commercial crops. In<br>most years, a few white flies can be seen<br>in the sesame with no economic damage.<br>In the middle 1990s, the USDA began<br>introducing natural predators of the<br>silverleaf white fly in the Uvalde area. It is<br>not known if the predators reduced the<br>effects of the white fly or there is a natural<br>tolerance to white fly in the current<br>varieties.<br>Higher temperatures decrease the<br>number of days between generations.<br>There are indications that higher moisture<br>and fertility increase the incidence of white<br>flies, but there is no definitive data.<br>The sweet potato white fly (Bemisia<br>tabaci) has been observed in nurseries<br>since 1978 without any economic damage. |
| (40) RESISTANCE TO<br>GREEN PEACH<br>APHIDS (*Myzus*<br>*persicae*)<br>Amount of resistance to<br>the green peach aphid | S32 = 5.50<br>(Uvalde nursery, 2004)<br>Subjective rating; see<br>Values for White Fly<br>Distribution within Sesaco<br>based on lines in Uvalde<br>nursery in 2004<br>(Total number of samples<br>tested = 412)<br>low = 1.00; high = 8.00<br>1 = <2.4; 1.0%<br>2 = <3.8; 0.5%<br>3 = <5.2; 10.7%<br>4 = <6.6; 4.8%<br>5 = >6.5; 83.0%<br>avg. = 7.04, std = 1.35 | See Methodology for RESISTANCE TO<br>SILVERLEAF WHITE FLY (Character No.<br>39)<br>COMMENTS: there have been very<br>few years (1990-1995) where the<br>incidence of green peach aphid has<br>affected nurseries or commercial crops. In<br>most years, a few aphids can be seen in<br>the sesame with no economic damage.<br>There have been many years in West<br>Texas when the cotton aphid has<br>decimated the cotton and did not build up<br>on adjacent sesame fields.<br>Higher moisture and fertility increase<br>the susceptibility to aphids. |
| (41) RESISTANCE TO<br>POD BORERS<br>(*Heliothis* spp.)<br>Amount of resistance to<br>pod borers | S32 = NT<br>Subjective rating; see<br>Values for White Fly | See Methodology for RESISTANCE TO<br>SILVERLEAF WHITE FLY (Character No.<br>39)<br>COMMENTS: there have been very<br>few years (1985) where the incidence of<br>*Heliothis* has affected nurseries or<br>commercial crops. In most years, a few<br>borers can be seen in the sesame with no<br>economic damage. |
| (42) RESISTANCE TO<br>ARMY WORMS<br>(*Spodoptera* spp.)<br>Amount of resistance to<br>army worms | S32 = NT<br>Subjective rating; see<br>Values for White Fly | See Methodology for RESISTANCE TO<br>SILVERLEAF WHITE FLY (Character No.<br>39)<br>COMMENTS: there have been very<br>few years (1984-1987) where the |

TABLE II-continued

Characters Distinguishing the S32 Line

| Character | Rating | Methodology |
|---|---|---|
| (43) RESISTANCE TO CABBAGE LOOPERS (*Pieris rapae*) Amount of resistance to cabbage loopers | S32 = NEC (Lorenzo nursery 2007) Subjective rating; see values for White Fly | incidence of *Spodoptera* has affected commercial crops in Arizona. In Texas, army worms have decimated cotton and alfalfa fields next to sesame without any damage to the sesame. It is not known if the Arizona army worm is different from the Texas army worm. See Methodology for RESISTANCE TO SILVERLEAF WHITE FLY (Character No. 39) COMMENTS: there have been very few years (1992-1993) where the incidence of cabbage loopers has affected nurseries. In commercial sesame, cabbage loopers have been observed with no economic damage. |

<sup>a</sup>Uvalde nursery planted north of Uvalde, Texas (latitude 29°22' north, longitude 99°47' west, 226 m elev) in middle to late May to early June from 1988 to the present; mean rainfall is 608 mm annually with a mean of 253 mm during the growing season; temperatures range from an average low of 3° C. and an average high of 17° C. in January to an average low of 22° C. and an average high of 37° C. in July. The nursery was planted on 96 cm beds from 1988 to 1997 and on 76 cm beds from 1998 to the present. The nursery was pre-irrigated and has had 2-3 post-plant irrigations depending on rainfall. The fertility has varied from 30-60 units of nitrogen.
<sup>b</sup>Lorenzo nursery planted southeast of Lubbock, Texas (latitude 33°40' north, longitude 101°49' west, 1000 m elev) in mid June from 2004 to the present; mean rainfall is 483 mm annually with a mean of 320 mm during the growing season; temperatures range from an average low of −4° C. and an average high of 11° C. in January to an average low of 20° C. and an average high of 33° C. in July. The nursery was planted on 101 cm beds. The nursery was rainfed. The fertility was 30 units of nitrogen.

In developing sesame varieties for the United States, there are seven characters that are desirable for successful crops: SHAKER SHATTER RESISTANCE (Character No. 22), IMPROVED NON-DEHISCENT VISUAL RATING (Character No. 25), COMPOSITE KILL RESISTANCE (Character No. 34), DAYS TO PHYSIOLOGICAL MATURITY (Character No. 29), SEED COLOR (Character No. 32), and SEED WEIGHT—100 SEEDS FROM 10CAP TEST (Character No. 33). The first four characters contribute to YIELD AT DRYDOWN (Character 10) which is the most important economic factor normally considered by a farmer in the selection of a variety. In improving the characters, the yields have to be comparable to or better than current varieties, or provide a beneficial improvement for a particular geographical or market niche. SHAKER SHATTER RESISTANCE and IMPROVED NON-DEHISCENT VISUAL RATING determine how well the plants will retain the seed while they are drying down in adverse weather.

COMPOSITE KILL RESISTANCE determines whether the plants can finish their cycle and have the optimum seed fill. DAYS TO PHYSIOLOGICAL MATURITY determines how far north and to which elevation the varieties can be grown. In the United States and Europe, the SEED COLOR is important since over 95% of the market requires white or buff seed. There are limited markets for gold and black seed in the Far East. All other colors can only be used in the oil market. SEED WEIGHT—100 SEEDS FROM 10CAP TEST determines the market for the seed. Lack of COMPOSITE KILL RESISTANCE can reduce SEED WEIGHT—100 SEEDS FROM 10CAP TEST. In parts of the United States where there is little rain in dry years and the lack of moisture can reduce the SEED WEIGHT—100 SEEDS FROM 10CAP TEST.

There are other characters important in developing commercial sesame varieties explained in Langham, D. R. and T. Wiemers, 2002. "Progress in mechanizing sesame in the US through breeding", In: J. Janick and A. Whipkey (ed.), *Trends in new crops and new uses*, ASHS Press, Alexandria, Va. BRANCHING STYLE (Character No. 1), HEIGHT OF PLANT (Character No. 5) and HEIGHT OF FIRST CAPSULE (Character No. 6) are important in combining. CAPSULE ZONE LENGTH (Character No. 7), NUMBER OF CAPSULE NODES (Character No. 8), AVERAGE INTERNODE LENGTH WITHIN CAPSULE ZONE (Character No. 9), and SEED WEIGHT PER CAPSULE (Character No. 18) are important in creating potential YIELD AT DRYDOWN (Character No. 10). LEAF DIMENSIONS (Characters No. 12, 13, 14, and 15) are important in determining optimum populations.

NUMBER OF CAPSULES PER LEAF AXIL (Character No. 2), NUMBER OF CARPELS PER CAPSULE (Character No. 16), CAPSULE LENGTH (Character No. 17), CAPSULE WEIGHT PER CAPSULE (Character No. 19), and CAPSULE WEIGHT PER CM OF CAPSULE (Character No. 20) are important in breeding for VISUAL SEED RETENTION (Character No. 21) and IMPROVED NON-DEHISCENT VISUAL RATING (Character No. 25) which lead to testing for SHAKER SHATTER RESISTANCE (Character No. 22) and determining the CAPSULE SHATTERING TYPE (Character No. 23), NON-DEHISCENT TEST (Character 24) and IMPROVED NON-DEHISCENT TEST (Character No. 26).

DAYS TO FLOWERING (Character No. 27), DAYS TO FLOWER TERMINATION (Character No. 28), DAYS TO PHYSIOLOGICAL MATURITY (Character No. 29), and MATURITY CLASS (Character No. 3) are highly correlated and important in determining the phenology and geographical range for the variety.

DAYS TO DIRECT HARVEST (Character No. 30) is important in that once the plants reach physiological maturity there is no weather event that will increase yield and many weather events that may substantially lower the yield. A shorter drying phase increases yield. PLANT PHENOTYPE (Character No. 4) is a summary character of characters 1, 2, and 3 that allows an overall visualization of the line.

RESISTANCE TO DROUGHT (Character No. 11) becomes important in reducing yield and seed weight. Even though there was a drought in the growing areas in 2006, there has not been a drought in nurseries planted since 2000 because of irrigation. LODGING RESISTANCE (Character No. 31) is important in years when there are high winds in the growing areas. The resistance characters (Characters No. 35, 36, 37, 38, 39, 40, 41, 42, and 43) are important in reducing the losses from diseases and pests.

Over the past 30 years, Sesaco has tested 2,966 introductions from all over the world. Commercial samples have been obtained from China, India, Sudan, Ethiopia, Burkina Faso, Nigeria, Mozambique, Pakistan, Myanmar, Bangladesh, Vietnam, Egypt, Mexico, Guatemala, Nicaragua, Venezuela, Thailand, Turkey, Upper Volta, Uganda, Mali, Kenya, Indonesia, Sri Lanka, Afghanistan, Philippines, Colombia, Ivory Coast, Gambia, Somalia, Eritrea, Paraguay, and El Salvador. Additional research seed has been received from the commercial countries and from many other countries such as Australia, Iraq, Iran, Japan, Russia, Jordan, Yemen, Syria, Morocco, Saudi Arabia, Angola, Argentina, Peru, Brazil, Cambodia, Laos, Sri Lanka, Ghana, Gabon, Greece, Italy, South Korea, Libya, Nepal, Zaire, England and Tanzania. Research seed received from one country may have originated from another unspecified country. All of the commercial and research introductions have CAPSULE SHATTERING TYPE (Character No. 23) of shattering, "SHA".

Using selected characters from Table II, Table III provides a character differentiation between S32 and name cultivars from all over the world.

TABLE III

Character Differentiation of Various Sesame Varieties[a]

| Character | Rating | Name cultivars tested by Sesaco |
|---|---|---|
| CAPSULE SHATTERING TYPE (Character No. 23) | SHA | Eliminate the following from the world: From Venezuela: Venezuela 51, Venezuela 52, Guacara, Aceitera, Inamar, Acarigua, Morada, Capsula Larga, Arawaca, Piritu, Glauca, Turen, DV9, Fonucla, UCLA From Mexico: Pachequeno, Yori, Anna, Teras, Denisse, Canasta, Tehvantepeter From India: TMV1, TMV3 From Turkey: Ozberk, Muganli, Gamdibi, Marmara From Israel: DT45 From Guatemala: R198, R30 From Paraguay: Escoba and INIA. From Texas: Llano, Margo, Dulce, Blanco, Paloma, Oro, Renner 1 and 2, Early Russian From California: UCR3, UCR4, Eva, Calinda (Cal Beauty) From Thailand: KU18 From Korea: Danback, Gwansan, Pungyiong, Suweon, Yuseong, Hanseon, Ahnsan, Kwangsan, Jinback, Pungsan, Sodan, Yangheuk, Konheuk, Whaheuck, Sungboon |
| | SSH | Eliminate from Sesaco: S02, S03, S04, S05, S06, S07, S08, S09, S10, S12, S14 |
| | ID | Eliminate the following from the world: From Venezuela: G2, Morada id From Texas: Rio, Delco, Baco, Improved Baco, Roy, Eli From South Carolina: Palmetto From California: UCR234 From Sesaco: S01 |
| | SR | All others, go to NON-DEHISCENT TEST |
| NON-DEHISCENT TEST (Character No. 24) | XX | Eliminate from Sesaco: S11, S15, S16, S17, S18, S19, S20, S21 |
| | ND | All others to the Improved NON-DEHISCENT TEST |
| IMPROVED NON-DEHISCENT TEST (Character No. 26) | ZZ | Eliminate from Sesaco: 11W, 19A, S22, S23, S24, S25, S26, S28, S29 (all of these lines and varieties have been disclosed in previous patents, and there are no lines or varieties that are not included.) |
| | IND | From Sesaco: S32 |

[a]SHA = shattering; SSH = semi-shattering; ID = indehiscent; SR = shatter resistant; XX = not non-dehiscent according to the teachings of U.S. Pat. No. 6,100,452; ND = non-dehiscent according to the teachings of U.S. Pat. No. 6,100,452; IND = improved non-dehiscent according to the teachings of U.S. Patent application Ser. No. _____ (Attorney Docket Number SESA 3200 PTUS)

Although Table III differentiates S32 from all other cultivars and varities, Table IV provides additional separation from two of the other current varities S25 and S29 and Table V shows all the characters from Table II for S32 and the other two current varieties S26 and S28.

TABLE IV

Character Comparison of S32 to S25 and S29

| No. | Character | Year/nursery | S25 | S29 | S32 |
|---|---|---|---|---|---|
| 5 | HEIGHT OF PLANT (cm) | 2007 UV | 130 | 138 | 147 |
| 6 | HEIGHT OF FIRST CAPSULE (cm) | 2007 UV | 65 | 56 | 58 |

TABLE IV-continued

Character Comparison of S32 to S25 and S29

| No. | Character | Year/nursery | S25 | S29 | S32 |
|---|---|---|---|---|---|
| 7 | CAPSULE ZONE LENGTH (cm) | 2007 UV | 65 | 82 | 89 |
| 17 | CAPSULE LENGTH (cm) | 1997-2006 All | 2.84 | 2.80 | 2.14 |

S32 is taller, has a longer capsule zone, and has shorter capsules than S25 and S29. There are other differences, but these clearly separate S32 from these two commercial varieties—S25 and S29.

Table V compares S32 to S26 and S28 because they are the closest phenotypically, and they share one common parent (031) that has many of the characters of the three varieties. The table is in terms of all of the characters listed in Table II. The major differences in Table V are indicated in the "Dif" column by a "C" for commercially important differences and an "M" for morphological differences.

TABLE V

Character Comparison of S26, S28, and S32[a]

| No. | Character | Year/nursery | S26 | S28 | S32 | Dif |
|---|---|---|---|---|---|---|
| 1 | BRANCHING STYLE | ALL | B | B | B | |
| 2 | NUMBER OF CAPSULES PER LEAF AXIL | ALL | 1 | 1 | 1 | |
| 3 | MATURITY CLASS | ADJUSTED PM | 100 | 99 | 97 | |
| | | 2005-2007 UV | M | M | M | |
| 4 | PLANT PHENOTYPE | ALL | B1M | B1M | B1M | |
| 5 | HEIGHT OF PLANT (cm) | 2007 UV | 148 | 144 | 147 | |
| 6 | HEIGHT OF FIRST CAPSULE (cm) | 2007 UV | 60 | 58 | 58 | |
| 7 | CAPSULE ZONE LENGTH (cm) | 2007 UV | 88 | 86 | 89 | |
| 8 | NUMBER OF CAPSULE NODES | 2007 UV | 31 | 29 | 25 | M |
| 9 | AVERAGE INTERNODE LENGTH WITHIN CAPSULE ZONE (cm) | 2007 UV | 2.9 | 3.0 | 3.6 | M |
| 10 | YIELD AT DRYDOWN (kg/ha) | 2007 UV | 1308 | 1384 | 1315 | |
| | | 2007 LO | 464 | 639 | 1059 | C |
| 11 | RESISTANCE TO DROUGHT | 2000 SA | GOOD | GOOD | NT | |
| 12 | LEAF LENGTH (cm) | $5^{th}$ - 2006 LO | 24.1 | 23.3 | NT | |
| | | $10^{th}$ - 2006 LO | 12.5 | 12.1 | NT | |
| | | $15^{th}$ - 2006 LO | 9.1 | 7.6 | NT | |
| 13 | LEAF BLADE LENGTH (cm) | $5^{th}$ - 2006 LO | 13.4 | 13.8 | NT | |
| | | $10^{th}$ - 2006 LO | 9.8 | 9.3 | NT | |
| | | $15^{th}$ - 2006 LO | 7.5 | 6.6 | NT | |
| 14 | LEAF BLADE WIDTH (cm) | $5^{th}$ - 2006 LO | 14.5 | 14.8 | NT | |
| | | $10^{th}$ - 2006 LO | 3.3 | 2.6 | NT | |
| | | $15^{th}$ - 2006 LO | 1.2 | 0.9 | NT | |
| 15 | PETIOLE LENGTH (cm) | $5^{th}$ - 2006 LO | 10.7 | 9.5 | NT | |
| | | $10^{th}$ - 2006 LO | 2.7 | 2.8 | NT | |
| | | $15^{th}$ - 2006 LO | 1.6 | 1.0 | NT | |
| 16 | NUMBER OF CARPELS PER CAPSULE | ALL | 2 | 2 | 2 | |
| 17 | CAPSULE LENGTH (cm) | 1997-2006 All | 2.24 | 2.25 | 2.14 | |
| 18 | SEED WEIGHT PER CAPSULE (g) | 1997-2006 All | 0.234 | 0.229 | 0.227 | |
| 19 | CAPSULE WEIGHT PER CAPSULE (g) | 1997-2006 All | 0.164 | 0.166 | 0.147 | |
| 20 | CAPSULE WEIGHT PER CM OF CAPSULE (g) | 1997-2006 All | 0.073 | 0.074 | 0.069 | |
| 21 | VISUAL SEED RETENTION | ALL | W | W | I | C |
| 22 | SHAKER SHATTER RESISTANCE (%) | 1997-2006 All | 72.9 | 75.3 | 77.2 | |
| 23 | CAPSULE SHATTERING TYPE | ALL | SR | SR | SR | |
| 24 | NON-DEHISCENT TEST | ALL | ND | ND | ND | |
| 25 | IMPROVED NON-DEHISCENT VISUAL RATING | 2006 UV | 6.33 | 6.33 | 7.33 | C |
| | | 2006 LO | 6.33 | 6.67 | 7.08 | C |
| | | 2007 LO | 6.56 | 6.56 | 7.35 | C |
| 26 | IMPROVED NON-DEHISCENT TEST | ALL | ZZ | ZZ | IND | C |
| 27 | DAYS TO FLOWERING | 2007 UV | 44 | 44 | 42 | |
| 28 | DAYS TO FLOWER TERMINATION | 2007 UV | 90 | 88 | 88 | |
| 29 | DAYS TO PHYSIOLOGICAL MATURITY | 2005-2007 UV | 100 | 99 | 97 | |
| | | 2005-2007 UV/LO | 104 | 103 | 102 | |
| | | 2007 UV | 109 | 108 | 108 | |
| 30 | DAYS TO DIRECT HARVEST | 2007 UV | 151 | 151 | 129 | C |
| 31 | LODGING RESISTANCE | 2007 UV | 6.43 | 7.00 | 6.28 | |
| | | 2007 LO | 5.00 | 5.25 | 7.08 | C |
| 32 | SEED COLOR | ALL | BF | BF | BF | |
| 33 | SEED WEIGHT - 100 SEEDS FROM 10CAP TEST (g) | 1997-2006 All | 0.331 | 0.331 | 0.312 | C |

TABLE V-continued

Character Comparison of S26, S28, and S32[a]

| No. | Character | Year/nursery | S26 | S28 | S32 | Dif |
|---|---|---|---|---|---|---|
| 34 | COMPOSITE KILL RESISTANCE | 2007 UV | 6.44 | 6.89 | 5.94 | C |
|  |  | 2007 LO | 6.25 | 6.50 | 6.25 | C |
| 35 | RESISTANCE TO FUSARIUM WILT (*F. oxysporum*) |  | NT | NT | NT |  |
| 36 | RESISTANCE TO PHYTOPHTORA STEM ROT (*P. parasitica*) | 2007 LO | NT | NT | NT |  |
| 37 | RESISTANCE TO CHARCOAL ROT (*Macrophomina phaseoli*) |  | NT | NT | NT |  |
| 38 | RESISTANCE TO BACTERIAL BLACK ROT (*Pseudomonas sesami*) | 2004 UV | 6.98 | 7.04 | 8.00 |  |
| 39 | RESISTANCE TO SILVERLEAF WHITE FLY (*Bemisia argentifolii*) | 2006 UV | NEC | NEC | NEC |  |
| 40 | RESISTANCE TO GREEN PEACH APHID (*Myzus persica*) | 2004 UV | 8.00 | 7.93 | 5.50 | C |
| 41 | RESISTANCE TO POD BORER (*Heliothis* spp.) | 2001 UV | NEC | NT | NT |  |
| 42 | RESISTANCE TO ARMY WORMS (*Spodoptera* spp.) |  | NT | NT | NT |  |
| 43 | RESISTANCE TO CABBAGE LOOPERS (*Pieris rapae*) | 2007 LO | NEC | NEC | NEC |  |

[a]B = true branches; U = uniculm (no true branches); UV = Uvalde nursery; M = medium maturity class of 95-104 days; B1M = phenotype of true branches, single capsules per leaf axil, and medium maturity class of 95-104 days; U1M = phenotype of uniculm, single capsules per leaf axil, and medium maturity class of 95-104 days; LO = Lorenzo nursery; NT = not tested; W = weather visual seed retention >75%; SR = shatter resistant; ND = non-dehiscent; ZZ = not improved non-dehiscent; IND = improved non-dehiscent; BF = buff color; and NEC = no economic damage - not enough disease or insects to do ratings.

As stated earlier, in developing sesame varieties for the United States, there are seven important characters: SHAKER SHATTER RESISTANCE (Character No. 22), IMPROVED NON-DEHISCENT VISUAL RATING (Character No. 25), COMPOSITE KILL RESISTANCE (Character No. 34), DAYS TO PHYSIOLOGICAL MATURITY (Character No. 29), YIELD AT DRYDOWN (Character No. 10), SEED COLOR (Character No. 32), and SEED WEIGHT—100 SEEDS FROM 10CAP TEST (Character No. 33). These characters will be discussed first and will include a discussion of all of the current commercial varieties (S25, S26, S28, S29, and S32), followed by other characters that differentiate S32 from S26 and S28.

FIG. 2 provides the SHAKER SHATTER RESISTANCE (Character No. 22) of all the varieties that have been harvested direct. S11 was the first variety that could be left standing for harvest with adequate yields in normal weather. With the exception of S17, varieties S15 through S22 were released for specific niches. S17 replaced S11 in most locations until it was replaced by S23 and S24. In 2001, S25 replaced S23. S23 is considered to be the minimum acceptable SHAKER SHATTER RESISTANCE for commercial use. S24, S25, S26, S28, and S29, all have SHAKER SHATTER RESISTANCE in the low to mid seventy percent level. S32 has a slightly higher SHAKER SHATTER RESISTANCE which contributes to a higher IMPROVED NON-DEHISCENT VISUAL RATING (Character No. 25).

Figure 3:
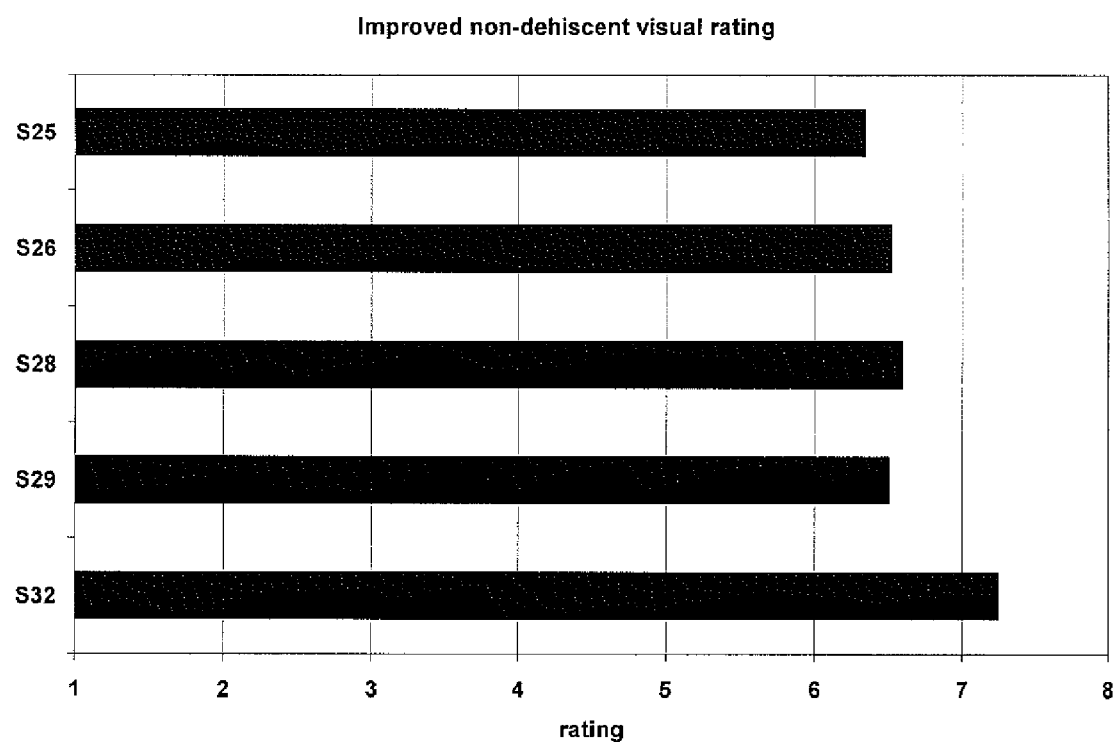
FIG. 3 depicts a comparison of the mean improved non-dehiscent visual rating from 2005 to 2007 for the current commercial varieties released by Sesaco.

FIG. 3 provides the IMPROVED NON-DEHISCENT VISUAL RATING (Character No. 25) of all of the present commercial varieties. SHAKER SHATTER RESISTANCE (Character No. 22) represents the amount of seed that is retained by the plant several months after being dry in the field. This standard was developed as a minimum standard in 1997-1998 and has proven to be a good predictor of shatter resistance. However, when the plants have reached DAYS TO DIRECT HARVEST (Character No. 30), the plants are holding more than the seed represented by the SHAKER SHATTER RESISTANCE percentage. If there is no rain, fog, dew, or wind during the drying phase, the plants will be retaining almost all of their seed for the combine. From the time that a capsule is dry the amount of shatter resistance begins to deteriorate. The IMPROVED NON-DEHISCENT VISUAL RATING sets a new benchmark for selecting varieties: the line has to have a rating of 7 or higher 4 weeks after DAYS TO DIRECT HARVEST (the ideal harvest time). S32 is the only commercial variety that meets this new standard as shown in FIG. 3 which is an average of 5 nurseries from 2005 to 2007.

Figure 4:
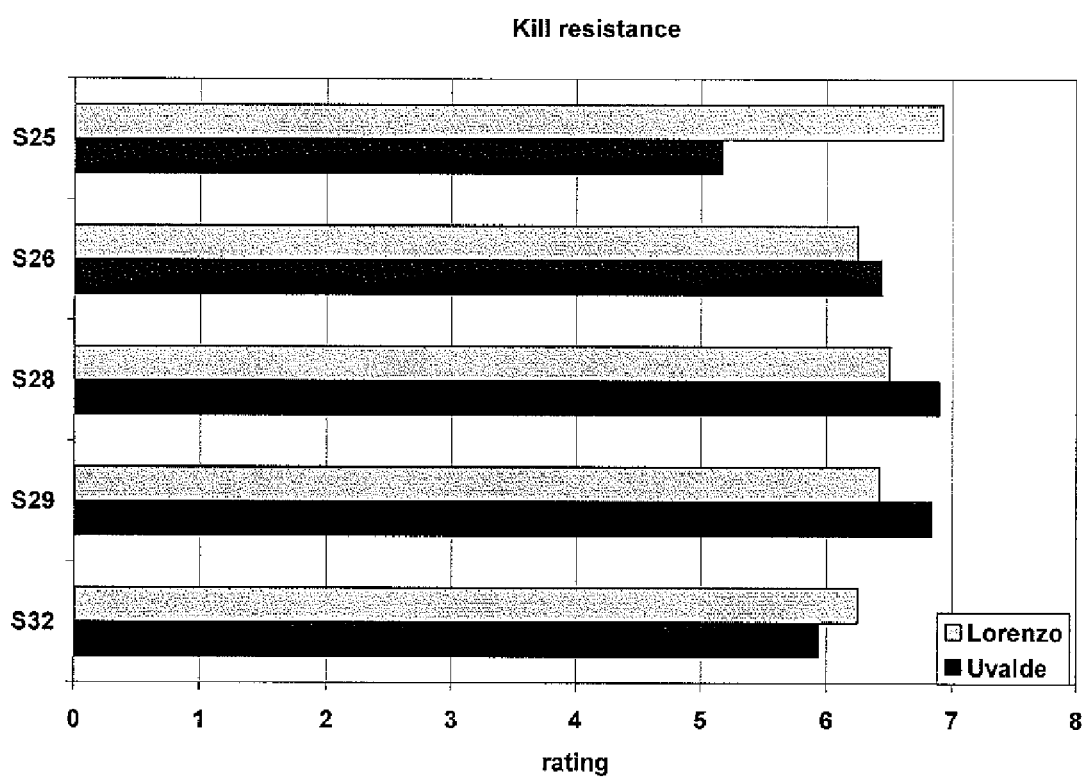
FIG. 4 depicts a comparison of the composite kill resistance ratings in Uvalde, Tex., and Lorenzo, Tex., in 2007 for the current commercial varieties released by Sesaco.

FIG. 4 provides the COMPOSITE KILL RESISTANCE (Character No. 34) of the current commercial varieties in the Uvalde and Lorenzo nurseries in 2007. COMPOSITE KILL RESISTANCE is a composite rating of resistance to three root rots: *Fusarium*, *Phytophtora*, and *Macrophomina*. In most years, *Fusarium* is the major cause of kill. When sesame is first introduced into a growing area, there are few disease problems, but over time the spores of these fungi accumulate and disease resistance becomes important. When sesame was first introduced in Uvalde in 1988, the yields were high. As farmers planted on the same fields in subsequent years, the yields decreased. S32 is slightly lower than S26, S28, and S29 in South Texas, but is comparable in North Texas. The ratings for S32 are acceptable for a commercial variety. Any rating above 5.67 indicates that over 90% of the plants produced good seed to the top of the plant.

Figure 5:
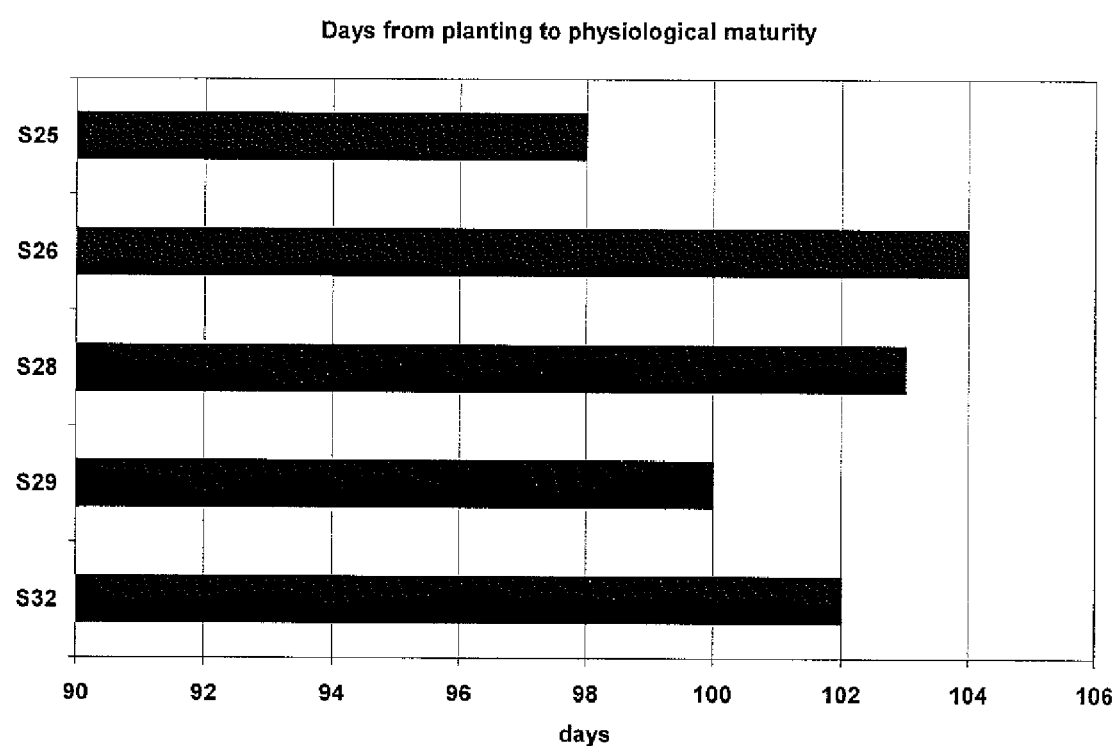
FIG. 5 depicts a comparison of the mean days to physiological maturity from 2005 to 2007 for the current commercial varieties released by Sesaco.

FIG. 5 provides the mean DAYS TO PHYSIOLOGICAL MATURITY (Character No. 29) of the current commercial varieties in 2005 to 2007 in the Uvalde and Lorenzo nurseries. In the United States, sesame is currently grown from South Texas to southern Kansas. The growing window of a crop is determined by the earliest the crop can be planted in the spring as the ground warms up, and the onset of cold weather in the fall. Current sesame varieties require about 21° C. ground temperature to establish an adequate population. In most years, the ground is warm enough in South Texas in middle April and in southern Kansas in late May. Current sesame varieties require night temperatures above 5° C. for normal termination. In most years, the night temperatures are warm enough in South Texas until middle November and in southern Kansas until middle October. There have been years when cold fronts affect the growth of sesame in the middle of September in the north. East of Lubbock, Tex., the elevations begin climbing towards the Rocky Mountains, and there are later warm temperatures in the spring and earlier cold temperatures in the fall. In all years, if the sesame is planted as early as temperatures allow, lines with DAYS TO PHYSIOLOGICAL MATURITY of 105 days or less will have no problems. However, most areas are rainfed, and it is essential to have a planting rain before planting the sesame. Thus, the earlier the DAYS TO PHYSIOLOGICAL MATURITY of the variety, the more flexibility the farmers have with planting date. In South Texas, the goal is to have varieties with a DAYS TO PHYSIOLOGICAL MATURITY of less than 110 days while in southern Kansas the goal is less than 90 days. The mean DAYS TO PHYSIOLOGICAL MATURITY for S32 from 2205 to 2007 is 102 which allows it to be planted in all of the current sesame growing areas.

Figure 6:
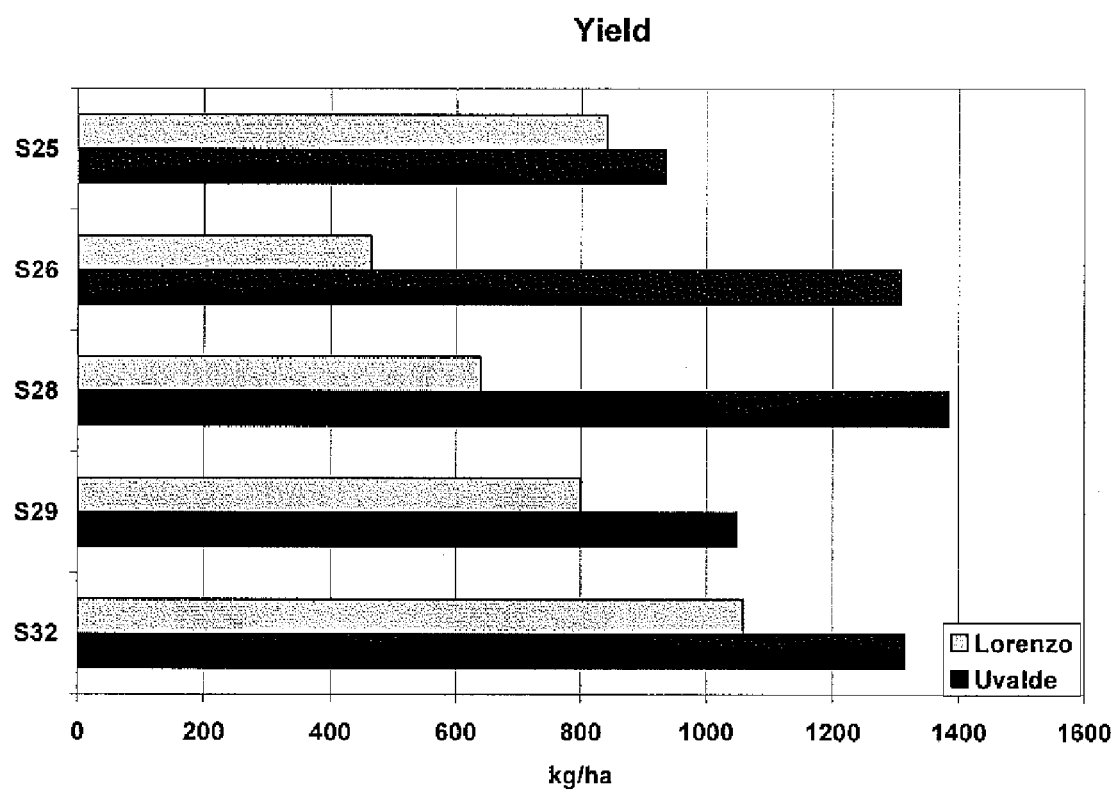
FIG. 6 depicts a comparison of the yield in Uvalde, Tex., and Lorenzo, Tex., in 2007 for the current commercial varieties released by Sesaco.

FIG. 6 provides the mean YIELD AT DRYDOWN (Character 10) in Uvalde and Lorenzo in 2007. In releasing a new variety, another important consideration is whether the yields (YIELD AT DRYDOWN) will be comparable or better than the existing varieties. In 2007 in the Uvalde irrigated nursery, S32 yield (1,315 kg/ha) was comparable to S26/S28 (1,308/1,384 kg/ha) and better than S25/S29 (936/1,049). In 2007 in the Lorenzo irrigated nursery, S32 yield (1,059 kg/ha) was considerably higher than all the commercial varieties: S25 with 841 kg/ha, S26 with 464, S28 with 639 and S29 with 800. S32 became a variety because the yields are comparable to the existing varieties in all conditions, and better under certain conditions.

Figure 7:
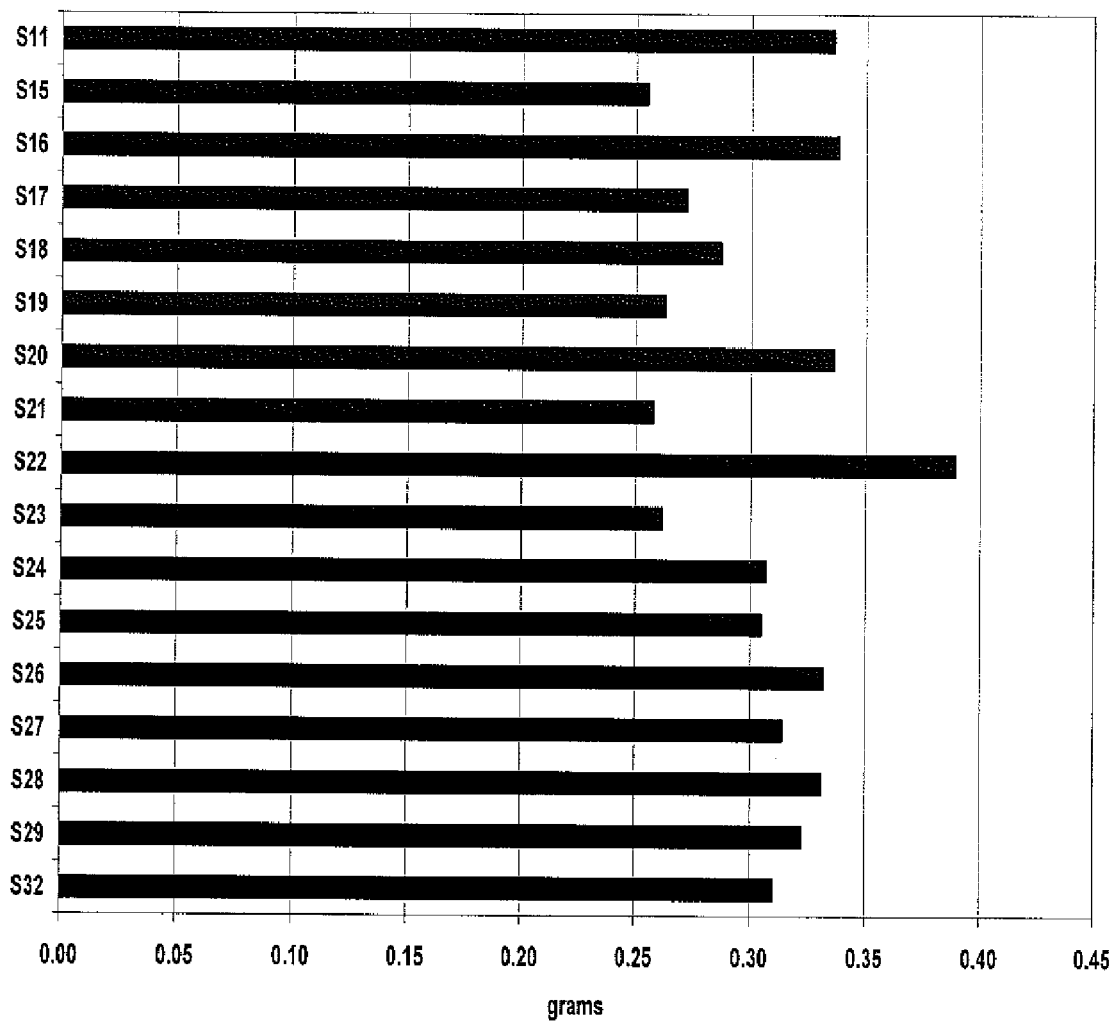
FIG. 7 depicts a comparison of the mean weight of 100 seeds in grams from 1997 to 2006 for the varieties released by Sesaco that have been used in direct harvest.

FIG. 7 provides the mean SEED WEIGHT—100 SEEDS FROM THE 10CAP TEST (Character No. 33) of all direct harvest varieties between 1997 and 2006. The hulled market is the premium use of sesame in the United States and Europe. In recent years, hulled sesame processors have been increasing the specifications of SEED WEIGHT—100 SEEDS FROM THE 10CAP TEST to between 0.33 and 0.35 g, with the larger seed preferable for hulled products used on top of breads and buns. To date, the Sesaco varieties with the highest SEED WEIGHT—100 SEEDS FROM THE 10CAP TEST have had marginal SHAKER SHATTER RESISTANCE (Character No. 22) and poor COMPOSITE KILL RESISTANCE (Character No. 34). Most markets have no specifications on seed weight, but larger seed is still desirable. The mean SEED WEIGHT—100 SEEDS FROM THE 10CAP TEST for S32 for all years is smaller than all the current varieties except S25, but still meets the specifications for a substantial portion of the U.S. market. Even if S32 were the only variety in the U.S., there is more than enough suitable market to use the entire crop.

SEED COLOR (Character No. 32) is the last important character and S32 is the same (buff) as the other commercial varieties.

The following paragraphs will discuss other characters that distinguish S32 from S26 and S28. First the commercial significant characters will be discussed, followed by the morphological characters.

DAYS TO DIRECT HARVEST (Character No. 30) is important because once the plants are mature, the faster the drydown period the shorter the time that the sesame field is exposed to bad weather conditions that yield loss. As discussed above, rain, fog, dew, and wind can reduce shatter resistance, and as will be discussed below, high winds can lead to lodging. The number of DAYS TO DIRECT HARVEST will vary depending on the environment, but generally a line that dries down faster than other lines in one environment will dry down faster in all environments. In the 2007 Uvalde nursery S32 dried down 22 days earlier than S26 and S28 enabling harvest three weeks earlier. This is a significant character which will help the average YIELD AT DRYDOWN (Character No. 10) over the other commercial varieties.

LODGING RESISTANCE (Character 31) must be measured when plants are subjected to significant wind events that demonstrate differences between the lines. Lines that lodge under low wind conditions are screened out of plant improvement programs and do not become candidates for varieties. S32 exhibits acceptable lodging resistance.

RESISTANCE TO GREEN PEACH APHID (*MYZUS PERSICA*) (Character No. 40) has been a marginally important character because aphids have been a rare problem in sesame in the U.S. Sesame is not susceptible to the more common cotton aphid (*Aphis gossypii*). At least one variety known to the inventor (S11) was very susceptible to the green peach aphid, and this susceptibility caused damage in two commercial fields. Limited data on S32 indicates it does not have increased resistance to green peach aphids and is comparable to standard lines.

NUMBER OF CAPSULE NODES (Character No. 8) and AVERAGE INTERNODE LENGTH WITHIN CAPSULE ZONE (Character No. 9) are usually related. The greater the number of capsule nodes, the shorter the internode length. S32 has fewer capsule nodes and longer internode length than S26 and S28, but still results in acceptable yields. The internode length is one of the characters that is used to visually distinguish S32 from the other two varieties in the field.

On Jan. 17, 2008, a deposit of at least 2500 seeds of sesame plant S32 was made by Sesaco Corporation under the provisions of the Budapest Treaty with the American Type Culture Collection (ATCC), 10801 University Boulevard, Manassas, Va. 20110-2209, and the deposit was given ATCC Accession No. PTA-8888. This deposit will be maintained in the ATCC depository for a period of 30 years or 5 years after the last request or for the enforceable life of the patent, whichever is longer. Should the seeds from the sesame line S32 deposited with the American Type Culture Collection become unviable, the deposit will be replaced by Sesaco Corporation upon request.

The foregoing invention has been described in some detail by way of illustration and characters for purposes of clarity and understanding. However, it will be obvious that certain changes and modifications may be practiced within the scope of the invention as limited only by the scope of the appended claims.

I claim:

1. A seed of sesame variety designated S32, a sample of said seed having been deposited under ATCC Accession No. PTA-8888.

2. A sesame plant produced by growing the seed of sesame variety S32, a sample of said seed having been deposited under ATCC Accession No. PTA-8888.

3. Pollen of said sesame plant of claim 2.

4. A sesame plant having all the physiological and morphological characteristics of sesame variety S32, a sample of the seed of said variety having been deposited under ATCC Accession No. PTA-8888.

5. A tissue culture of regenerable cells produced from seed of sesame variety S32, a sample of said seed having been deposited under ATCC Accession No. PTA-8888.

6. A tissue culture of regenerable cells produced from sesame plant S32 produced by growing the seed of sesame variety S32, a sample of said seed having been deposited under ATCC Accession No. PTA-8888.

7. A sesame plant regenerated from a tissue culture of regenerable cells produced from seed of sesame variety S32, a sample of said seed having been deposited under ATCC Accession No. PTA-8888, wherein said regenerated sesame plant has all the physiological and morphological characteristics of said sesame variety S32.

8. A sesame plant regenerated from a tissue culture of regenerable cells produced from a sesame plant produced by growing the seed of sesame variety S32, a sample of said seed having been deposited under ATCC Accession No. PTA-8888, wherein said regenerated sesame plant has all the physiological and morphological characteristics of said sesame variety S32.

9. A method of producing sesame seed, comprising crossing a first parent sesame plant with a second parent sesame plant and harvesting the resultant sesame seed, wherein said first or second parent sesame plant was produced by growing seed of sesame variety S32, a sample of said seed having been deposited under ATCC Accession No. PTA-8888.

* * * * *

UNITED STATES PATENT AND TRADEMARK OFFICE
CERTIFICATE OF CORRECTION

PATENT NO.        : 7,855,317 B2
APPLICATION NO.   : 12/041205
DATED             : December 21, 2010
INVENTOR(S)       : Derald Ray Langham It is certified that error appears in the above-identified patent and that said Letters Patent is hereby corrected as shown below:

Col. 7, line 2, replace "X11" with -- X111 --
Col. 8, line 57, replace "Weilton" with -- Wellton --
Col. 8, line 61, replace "Weliton" with -- Wellton --
Col. 9, line 19, replace "TSM" with -- TSAA --
Col. 9, line 20, replace "(3)" with -- (31) --
Col. 10, line 13, replace "plant all" with -- plant having all --
Col. 20, Table II, under "Methodology," column text line 40, replace "Character No. 13)" with -- (Character No. 13) --
Col. 23, Table II, under "Rating," column text line 48, replace "number" with -- number) --
Col. 30, Table II, under "Methodology," column text line 10, replace "causing there is" with -- causing --
Col. 30, Table II, under "Methodology," column text line 31, replace "dry down" with -- drydown --
Col. 31, Table II, under "Character," column text line 12, replace "____" with -- 12/041,257, filed March 3, 2008 --
Col. 31, Table II, under "Rating," column text line 13, replace "'eg'" with -- e.g. --
Col. 31, Table II, under "Rating," column text line 21, replace ">7.5;" with -- >7.4; --
Col. 32, Table II, under "Methodology," column text line 2, replace "counts" with -- count --
Col. 32, Table II, under "Methodology," column text line 21, replace "a ratings" with -- ratings --
Col. 33, Table II, under "Rating," column text line 28, replace "102.2" with -- <102.2 --
Col. 33, Table II, under "Rating," column text line 43, replace "tthrough" with -- through --
Col. 34, Table II, under "Methodology," column text line 19, replace "to shorter" with -- to a shorter --
Col. 36, Table II, under "Methodology," column text line 73, replace "normally only" with -- are normally only --
Col. 37, Table II, under "Rating," column text line 48, replace "<0..251" with -- <0.251 --
Col. 38, Table II, under "Methodology," column text line 44, replace "parasitica." with -- *parasitica.* --
Col. 39, Table II, under "Character," column text line 2, replace "FUSARIUMWILT" with -- *FUSARIUM* WILT --

Signed and Sealed this
Twenty-third Day of October, 2012

David J. Kappos
*Director of the United States Patent and Trademark Office*

Col. 39, Table II, under "Character," column text line 19, replace "sesami)" with -- *sesami)* --

Col. 42, Table II, under "Methodology," column text line 27-28, replace "(Bemisia tabaci)" with -- *(Bemisia tahaci)* --

Col. 51, line 18, replace "2205" with -- 2005 --